(12) United States Patent
Schnider

(10) Patent No.: US 8,642,590 B2
(45) Date of Patent: Feb. 4, 2014

(54) ALKYLCYCLOHEXYLETHERS OF DIHYDROTETRAAZABENZOAZULENES

(75) Inventor: Patrick Schnider, Bottmingen (CH)

(73) Assignee: Hoffmann-La Roche Inc., Nutley, NJ (US)

(*) Notice: Subject to any disclaimer, the term of this patent is extended or adjusted under 35 U.S.C. 154(b) by 838 days.

(21) Appl. No.: 12/616,805

(22) Filed: Nov. 12, 2009

(65) Prior Publication Data
US 2010/0125066 A1   May 20, 2010

(30) Foreign Application Priority Data
Nov. 18, 2008 (EP) .................................. 08169348

(51) Int. Cl.
*A61P 9/00* (2006.01)
*A61K 31/55* (2006.01)
*C07D 487/12* (2006.01)

(52) U.S. Cl.
USPC ........................................ 514/220; 540/563

(58) Field of Classification Search
USPC ........................................ 514/220; 540/563
See application file for complete search history.

(56) References Cited

U.S. PATENT DOCUMENTS

| 7,265,104 B2 | 9/2007 | Elliott et al. |
| 2002/0103373 A1 | 8/2002 | Hoekstra et al. |
| 2011/0245237 A1 | 10/2011 | Dolente et al. |
| 2011/0251183 A1 | 10/2011 | Dolente et al. |
| 2011/0263573 A1 | 10/2011 | Dolente et al. |
| 2011/0263578 A1 | 10/2011 | Dolente et al. |
| 2011/0275801 A1 | 11/2011 | Dolente et al. |

FOREIGN PATENT DOCUMENTS

| EP | 2292621 | 3/2011 |
| JP | 2004-231668 | 8/2004 |
| KR | 2007/0020462 | 2/2007 |
| WO | 96/22292 | 7/1996 |
| WO | 02/40487 | 5/2002 |
| WO | 02/083681 | 10/2002 |
| WO | 2004/060894 | 7/2004 |
| WO | 2004074291 | 9/2004 |
| WO | 2005/040169 | 6/2005 |
| WO | 2005068466 | 7/2005 |
| WO | 2006021882 | 3/2006 |
| WO | 2006/097391 | 9/2006 |
| WO | 2006/114706 | 11/2006 |
| WO | 2006123242 | 11/2006 |
| WO | 2008084005 | 7/2008 |
| WO | 2010/057795 | 5/2010 |

OTHER PUBLICATIONS

Robben et al., (2006) Am. J. Physiol. Renal. Physiol. vol. 291, pp. F257-F270.
Neumann, (2008) J. Neuroendocrinol. vol. 20, pp. 858-865.
Ebner et al., (2002) Eur. J. Neurosci. vol. 15, pp. 384-388.
Kendler et al., (2003) Arch. Gen. Psychiatry vol. 60, pp. 789-796.
Regier et al., (1998) Br. J. Psychiatry Suppl. pp. 24-28.
Bielsky et al., (2004) Neuropsychopharmacology vol. 29, pp. 483-493.
Landgraf et al., (1995) Regul. Pept. vol. 59 pp. 229-239.
Yirmiya et al., (2006) vol. 11 pp. 488-494.
Thompson et al., (2004) Psychoneuroendocrinology vol. 29 pp. 35-48.
Raskind et al., (1987) Biol. Psychiatry vol. 22 pp. 453-462.
Altemus et al. (1992) Arch. Gen. Psychiatry vol. 49, pp. 9-20.
Michelini et al. (1999) Ann. NY Acad. Sci. vol. 897 pp. 198-211.
Van Kerckhoven et al., (2002) Eur. J. Pharmacol. vol. 449 pp. 135-141.
Brouard et al., (2000) Bjog. vol. 107 pp. 614-619.
Aughton et al., (2008) Br. J. Pharmacol. p. 253.
Gupta et al. (2008) Br. J. Pharmacol. vol. 155, pp. 118-126.
Gal et al., Progress in Brain Research, Elsevier 139:197-210 XP001205440 (2002).
(International Search Report for PCT/EP2011/057368 Jul. 14, 2011).
(International Search Report PCT/EP2011/056391 Jun. 27, 2011).
(International Search Report PCT/EP2011/056071 May 12, 2011).
(International Search Report for PCT/EP2011/054582 Mar. 25, 2011).
(International Search Report PCT/EP2009/065354 Feb. 8, 2010).
Liebsch et al., Regulatory Peptides 59(2):229-239 (1995).
(International Search Report PCT/EP2011/055516 May 23, 2011).
(Opposition in Costa Rican Appl. No. 2011-0220 Sep 20, 2011).
The Japanese Office Action, issued on May 14, 2013, in the corresponding Japanese application No. 2011-535980., pp. 5.
The Chinese Office Action, issued on Apr. 1, 2013, in corresponding Chinese application No. 200980146033.4., pp. 9.

*Primary Examiner* — Brenda Coleman

(57) ABSTRACT

The present invention is concerned with alkylcyclohexylethers of dihydro-tetraazabenzoazulenes, i.e. alkylcyclohexylethers of 5,6-dihydro-4H-2,3,5,10b-tetraaza-benzo[e]azulene s of formula I

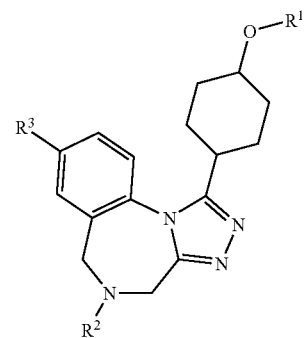

wherein $R^1$, $R^2$ and $R^3$ are as described herein, their manufacture, and pharmaceutical compositions containing them. The compounds according to the invention act as V1a receptor modulators, and in particular as V1a receptor antagonists. The compounds are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

17 Claims, No Drawings

ALKYLCYCLOHEXYLETHERS OF DIHYDROTETRAAZABENZOAZULENES

PRIORITY TO RELATED APPLICATION(S)

This application claims the benefit of European Patent Application No. 08169348.3, filed Nov. 18, 2008, which is hereby incorporated by reference in its entirety.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class 1 G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor can therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviours in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J Neurosci. 15, 384-8., "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al. (2004), Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Mad Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhoea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

SUMMARY OF THE INVENTION

The present invention provides alkylcyclohexylethers of dihydro-tetraazabenzoazulenes, i.e. alkylcyclohexylethers of 5,6-dihydro-4H-2,3,5,10b-tetraaza-benzo[e]azulenes, which act as V1a receptor modulators, and in particular as V1a receptor antagonists, their manufacture, pharmaceutical compositions containing them and their use for the treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

In particular, the present invention is concerned with alkylcyclohexylethers of dihydro-tetraazabenzoazulenes of formula I

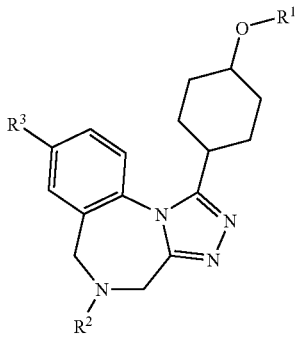

wherein

R¹ is C₁₋₁₂-alkyl, unsubstituted or substituted with one or more halo, hydroxy, cyano or C₁₋₁₂-alkoxy, C₃₋₇-cycloalkyl, unsubstituted or substituted by one or more substituents independently selected from B, or 4-7 membered heterocycloalkyl containing one or two heteroatoms selected from O, N and S, which heterocycloalkyl is unsubstituted or substituted by one or more substituents independently selected from B;

R² is H,

C₁₋₁₂-alkyl, unsubstituted or substituted with one or more OH, halo, cyano or C₁₋₁₂-alkoxy, —(CH₂)_q—Rᵃ, wherein Rᵃ is phenyl or 5- or 6-membered heteroaryl, each of which is unsubstituted or substituted with one or more substituents independently selected from A, —(CH₂)_rNRⁱRⁱⁱ, —C(O)—C₁₋₁₂-alkyl, wherein alkyl is unsubstituted or substituted with one or more OH, halo, cyano or C₁₋₁₂-alkoxy, —C(O)(CH₂)_qOC(O)—C₁₋₁₂-alkyl, —C(O)(CH₂)_qNRⁱRⁱⁱ, —C(O)O—C₁₋₁₂-alkyl, wherein alkyl is unsubstituted or substituted with one or more OH, halo, cyano or C₁₋₁₂-alkoxy, —S(O)₂—C₁₋₁₂-alkyl, or

—S(O)₂NRⁱRⁱⁱ;

Rⁱ and Rⁱⁱ are each independently H, C₁₋₁₂-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B;

q is 1, 2, 3 or 4;

r is 2, 3 or 4;

A is halo, cyano, OH, C₁₋₇-alkyl, halo-C₁₋₇-alkyl, or C₁₋₇-alkoxy;

B is oxo, halo, OH, C₁₋₇-alkyl or C₁₋₇-alkoxy; and

R³ is Cl or F;

or a pharmaceutically acceptable salt thereof.

DETAILED DESCRIPTION OF THE INVENTION

The present invention provides compounds which act as V1a receptor modulators, and in particular as V1a receptor antagonists. The invention further provides selective inhibitors of the V1a receptor since it is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. The preferred indications with regard to the present invention are the treatment of anxiety, depressive disorders, obsessive compulsive disorder, autistic spectrum disorders, schizophrenia, and aggressive behavior.

The V1a activity can be detected as described in the pharmaceutical test section.

The following definitions of the general terms used in the present description apply irrespective of whether the terms in question appear alone or in combination.

As used herein, the term "alkyl", alone or in combination with other groups, denotes a saturated, i.e. aliphatic, hydrocarbon group including a straight or branched carbon chain. If not further specified, "alkyl" groups denote groups with 1 to 12 carbon atoms, for example "C₁₋₁₂-alkyl". "C₁₋₄-alkyl" denotes alkyl groups with 1 to 4 carbon atoms and "C₁₋₇-alkyl" denotes alkyl groups with 1 to 7 carbon atoms. Examples of "alkyl" groups are methyl, ethyl, propyl, isopropyl, n-butyl, iso-butyl, sec-butyl, tert-butyl and the like. Preferred alkyl groups are methyl and i-propyl.

The term "alkoxy", alone or in combination with other groups, denotes a group —O—R' wherein R' is alkyl as defined above. "C₁₋₁₂-alkoxy" denotes alkoxy groups with 1 to 12 carbon atoms, "C₁₋₄-alkoxy" denotes alkoxy groups with 1 to 4 carbon atoms, and "C₁₋₇-alkoxy" denotes alkoxy groups with 1 to 7 carbon atoms. Examples of "alkoxy" groups are methoxy, ethoxy, propoxy, tert-butoxy and the like. A preferred alkoxy group is methoxy.

The term "aromatic" means the presence of an electron sextet in a ring, according to Hückel's rule.

The term "cyano" denotes the group —CN.

The term "hydroxy" denotes the group —OH.

The term "halo" or "halogen" denotes chloro, iodo, fluoro and bromo. Preferred are chloro and fluoro.

The terms "halo-C₁₋ₙ-alkyl" and "C₁₋ₙ-haloalkyl", alone or in combination with other groups, denote a C₁₋ₙ-alkyl group as defined above, with 1 to n carbon atoms as defined in the specification, wherein at least one of the hydrogen atoms of the alkyl group is replaced by a halogen atom, preferably fluoro or chloro, most preferably fluoro. Examples of halo-C₁₋ₙ-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below.

Among the preferred halo-C₁₋ₙ-alkyl groups are difluoro- or trifluoro-methyl or ethyl as well as —CF₃, —CH(CH₃) CH₂CF₃, and —CH(CH₃)CH₂F.

The term "heterocycloalkyl", alone or in combination with other groups, as defined herein refers to a monovalent 3 to 7 membered or 4 to 7 membered saturated ring containing one or two heteroatoms selected from N, O and S. The term "3- to 7-membered heterocycloalkyl", alone or in combination with other groups, as defined herein refers to a monovalent 3 to 7 membered ring containing one or two heteroatoms selected from N, O and S. The term "4-7 membered heterocycloalkyl", alone or in combination with other groups, refers to a 4 to 7 membered saturated ring containing one or two heteroatoms selected from N, O and S. Examples of heterocycloclakyl moieties are oxetanyl, tetrahydrofuranyl, tetrahydropyranyl, pyrrolidinyl, morpholinyl, thiomorpholinyl, piperidinyl, or piperazinyl. Preferred heterocycloalkyl are oxetanyl and tetrahydrofuranyl. Heterocycloalkyl is optionally substituted as described herein.

The terms "heteroaryl" and "5- or 6-membered heteroaryl", alone or in combination with other groups, refer to a monovalent aromatic 5- or 6-membered monocyclic ring containing one or two ring heteroatoms selected from N, O, and S, the remaining ring atoms being C. 6-Membered heteroaryl are preferred. Examples of heteroaryl moieties include but are not limited to pyridinyl, pyrimidinyl, and pyrazinyl. A preferred heteroaryl group is pyridinyl.

The terms "cycloalkyl" and "$C_{3-7}$-cycloalkyl", alone or in combination with other groups, refer to a 3 to 7 membered aliphatic carbon ring, for example cyclopropyl, cyclobutyl, cyclopentyl or cyclohexyl.

The term "oxo" when referring to substituents on heterocycloalkyl means that an oxygen atom is attached to the heterocycloalkyl ring. The "oxo" either replaces two hydrogen atoms on a carbon atom, or is attached to sulfur, so that the sulfur exists in oxidized form, i.e. bearing one or two oxygens like the group —$SO_2$.

When indicating the number of substituents, the term "one or more" means from one substituent to the highest possible number of substitution, i.e. replacement of one hydrogen up to replacement of all hydrogens by substituents. Thereby, one, two or three substituents are preferred. Even more preferred are one or two substituents or one substituent.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like. Preferred is the hydrochloric acid salt.

"Therapeutically effective amount" means an amount that is effective to prevent, alleviate or ameliorate symptoms of disease or prolong the survival of the subject being treated.

In detail, the present invention is concerned with alkylcyclohexylethers of dihydro-tetraazabenzoazulenes of formula I

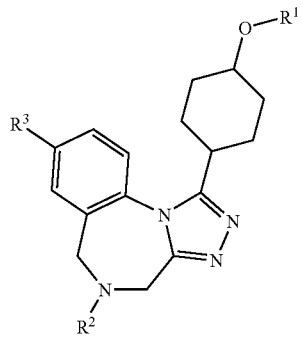

wherein
$R^1$ is $C_{1-12}$-alkyl, unsubstituted or substituted with one or more halo, hydroxy, cyano or $C_{1-12}$-alkoxy,
$C_{3-7}$-cycloalkyl, unsubstituted or substituted by one or more substituents independently selected from B, or
4-7 membered heterocycloalkyl containing one or two heteroatoms selected from O, N and S, which heterocycloalkyl is unsubstituted or substituted by one or more substituents independently selected from B;
$R^2$ is H,
$C_{1-12}$-alkyl, unsubstituted or substituted with one or more OH, halo, cyano or $C_{1-12}$-alkoxy,
—$(CH_2)_q$—$R^a$, wherein $R^a$ is phenyl or 5- or 6-membered heteroaryl, each of which is unsubstituted or substituted with one or more substituents independently selected from A,
—$(CH_2)_r NR^i R^{ii}$,
—C(O)—$C_{1-12}$-alkyl, wherein alkyl is unsubstituted or substituted with one or more OH, halo, cyano or $C_{1-12}$-alkoxy
—C(O)($CH_2)_q$OC(O)—$C_{1-12}$-alkyl,
—C(O)($CH_2)_q NR^i R^{ii}$,
—C(O)O—$C_{1-12}$-alkyl, wherein alkyl is unsubstituted or substituted with one or more OH, halo, cyano or $C_{1-12}$-alkoxy,
—$S(O)_2$—$C_{1-12}$-alkyl, or
—$S(O)_2 NR^i R^{ii}$, $R^i$ and $R^{ii}$ are each independently H, $C_{1-12}$-alkyl, or form together with the nitrogen to which they are bound a 3- to 7-membered heterocycloalkyl containing one or two heteroatoms selected from N, O or S, which heterocycloalkyl is unsubstituted or substituted by one or more substituents independently selected from B;
q is 1, 2, 3 or 4;
r is 2, 3 or 4;
A is halo, cyano, OH, $C_{1-7}$-alkyl, halo-$C_{1-7}$-alkyl, or $C_{1-7}$-alkoxy;
B is oxo, halo, OH, $C_{1-7}$-alkyl or $C_{1-7}$-alkoxy; and
$R^3$ is Cl or F;
or a pharmaceutically acceptable salt thereof.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| abbreviations | |
|---|---|
| $(BOC)_2O$ | di-tert-butyl dicarbonate |
| AcOH | acetic acid |
| brine | saturated sodium chloride solution in water |
| $CH_2Cl_2$ | dichloromethane |
| $CH_3I$ | methyl iodide |
| $CS_2$ | carbon disulfide |
| DMAP | 4-(dimethylamino)-pyridine |
| DMF | N,N-dimethylformamide |
| EDTA | ethylendiamin-tetraacetate |

TABLE 1-continued abbreviations

| | |
|---|---|
| EI | Electron ionization |
| Et₃N | triethylamine |
| Et₃SiH | triethylsilane |
| HEPES | 4-(2-hydroxyethyl)-1-piperazineethanesulfonic acid |
| HF | hydrofluoric acid |
| HPLC | high performance liquid chromatography |
| Lawesson's reagent | 2,4-bis(4-methoxyphenyl)-1,3,2,4-dithiadiphosphetane-2,4-disulfide |
| MeOH | methanol |
| MgClO₄ | magnesium perchlorate |
| MS | mass spectroscopy |
| NaH | sodium hydride |
| NaOH | sodium hydroxide |
| NBS | N-bromosuccinimide |
| n-BuOH | n-butanol |
| NMR | nuclear magnetic resonance |
| RNA | ribonucleic acid |
| RT | room temperature |
| RT-PCR | reverse-transcriptase polymerase chain reaction |
| SOCl₂ | thionyl chloride |
| T-BuOK, KOtBu | potassium tert butanolat |
| THF | tetrahydrofurane |
| TMSCl | trimethylsilyl chloride |
| TMSOTf | trimethylsilyl trifluoromethanesulfonate |
| Tris | aluminium-tris(8-hydroxychinolin |
| TsCl | toluene-2-sulfonyl chloride |
| ZnBr₂ | zinc bromide |

The invention also provides pharmaceutical compositions, methods of using, and methods of preparing the aforementioned compounds.

The compounds of formula I can contain asymmetric carbon atoms. Accordingly, the present invention includes all stereoisomeric forms of the compounds of formula I, including each of the individual stereoisomer and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the alkylcyclohexylether-head group (HG) of the compounds of formula I, namely

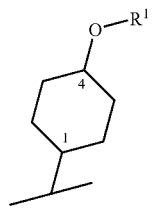

HG wherein at least the carbon atoms 1 and 4 are asymmetric carbon atoms and $R^1$ could further comprise asymmetric carbon atoms. It is to be understood that present invention includes all individual stereoisomers of head groups and mixtures thereof.

In particular, these head groups HG are

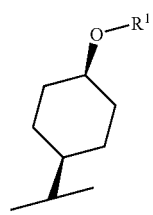

HG-1

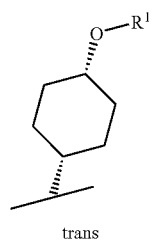

HG-2 trans

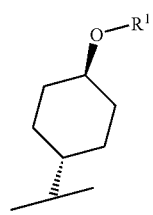

HG-3

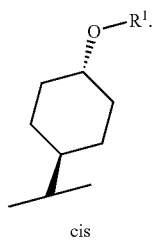

HG-4 cis

It is further understood that all embodiments of the invention as described herein can be combined with each other.

In certain embodiments, $R^1$ is as described above.

In certain embodiments, $R^1$ is $C_{1-12}$-alkyl, unsubstituted or substituted with one or more halo, hydroxy, cyano or $C_{1-12}$- alkoxy. In certain embodiments, $R^1$ is $C_{1-12}$-alkyl, unsubstituted or substituted with one or more halo, hydroxy or $C_{1-12}$-alkoxy.

In certain embodiments, $R^1$ is $C_{3-7}$ cycloalkyl, unsubstituted or substituted by one or more substituents independently selected from B, wherein B is oxo, halo, OH, $C_{1-7}$-alkyl or $C_{1-7}$-alkoxy. In certain embodiments, $R^1$ is $C_{3-7}$ cycloalkyl.

In certain embodiments, $R^1$ is 4-7 membered heterocycloalkyl containing one or two heteroatoms selected from O, N and S, which heterocycloalkyl is unsubstituted or substituted by one or more B and B is oxo, halo, OH, $C_{1-7}$-alkyl or $C_{1-7}$-alkoxy. In certain embodiments, the 4-7 membered heterocycloalkyl contains one or two heteroatoms selected from O and S, preferably one O, which heterocycloalkyl is unsubstituted or substituted by one or more oxo, halo, OH, $C_{1-7}$-alkyl or $C_{1-7}$-alkoxy. In certain embodiments, the heterocycloalkyl is oxetanyl or tetrahydropyranyl.

In certain embodiments,
$R^1$ is $C_{1-12}$-alkyl, unsubstituted or substituted with one or more halo, hydroxy or $C_{1-12}$-alkoxy, $C_{3-7}$ cycloalkyl, or
4-7 membered heterocycloalkyl containing one or two heteroatoms selected from O or S, preferably one O, which heterocycloalkyl is unsubstituted or substituted by one or more oxo, halo, OH, $C_{1-7}$-alkyl or $C_{1-7}$-alkoxy, preferably unsubstituted.

In certain embodiments, $R^1$ is —$CF_3$, —$CH(CH_3)CH_2CF_3$, —$CH(CH_3)CH_2F$, —$CH(CH_3)CH_2OH$, —CH($CH_3$)$CH_2OMe$, cyclobutyl, cyclohexyl, cyclopentyl, ethyl, i-propyl, methyl, oxetanyl, sec-butyl, t-butyl or tetrahydropyranyl.

In certain embodiments, $R^1$ is $C_{1-12}$-alkyl or $C_{3-7}$ cycloalkyl.

In certain embodiments, $R^1$ is i-propyl, cyclobutyl or cyclopentyl.

In certain embodiments, $R^1$ is unsubstituted $C_{1-12}$-alkyl.
In certain embodiments, $R^1$ is methyl.
In certain embodiments, $R^1$ is ethyl.
In certain embodiments, $R^1$ is isopropyl.
In certain embodiments, $R^1$ is sec-butanyl.
In certain embodiments, $R^1$ is t-butanyl.
In certain embodiments, $R^1$ is $C_{1-12}$-alkyl substituted with one or more halo.
In certain embodiments, $R^1$ is $CF_3$.
In certain embodiments, $R^1$ is $CH(CH_3)CH_2CF_3$.
In certain embodiments, $R^1$ is —$CH(CH_3)CH_2CF_3$.
In certain embodiments, $R^1$ is $C_{1-12}$-alkyl substituted with one or more hydroxy.
In certain embodiments, $R^1$ is —$CH(CH_3)CH_2OH$.
In certain embodiments, $R^1$ is $C_{1-12}$-alkyl substituted with one or more $C_{1-12}$-alkoxy.
In certain embodiments, $R^1$ is —$CH(CH_3)CH_2OH$.
In certain embodiments, $R^1$ is $C_{3-7}$ cycloalkyl.
In certain embodiments, $R^1$ is cyclobutyl.
In certain embodiments, $R^1$ is cyclohexyl.
In certain embodiments, $R^1$ is cyclopentyl.
In certain embodiments, $R^1$ is 4-7 membered heterocycloalkyl containing one or two heteroatoms selected from O and S, preferably one O, which heterocycloalkyl is unsubstituted.
In certain embodiments, $R^1$ is oxetanyl.
In certain embodiments, $R^1$ is tetrahydro-pyranyl.
In certain embodiments, $R^2$ is as described above.
In certain embodiments, $R^2$ is
H,
$C_{1-12}$-alkyl, unsubstituted or substituted with one or more OH,
—$(CH_2)_q$—$R^a$ wherein $R^a$ is phenyl or 5- or 6-membered heteroaryl and q is 1, 2, 3 or 4,
—C(O)—$C_{1-12}$-alkyl wherein alkyl is unsubstituted or substituted with one or more OH,
—C(O)($CH_2)_qOC(O)$—$C_{1-12}$-alkyl wherein q is 1, 2, 3 or 4,
—C(O)O—$C_{1-12}$-alkyl,
—S(O)$_2$—$C_{1-12}$-alkyl, or
—S(O)$_2NR^iR^{ii}$, wherein $R^i$ and $R^{ii}$ are each independently H or $C_{1-12}$-alkyl.

In certain embodiments, $R^2$ is $C_{1-12}$-alkyl.
In certain embodiments, $R^2$ is 2-hydroxy-ethyl, —C(O)$CH_2OC(O)$methyl, —C(O)hydroxymethyl, —C(O)methyl, —C(O)O-t-butyl, —$CH_2$-pyridin-2-yl, H, i-propyl, methyl, —S(O)$_2$methyl or —S(O)$_2$N(methyl)$_2$.

In certain embodiments, $R^2$ is H, thereby forming either the free base or a pharmaceutically acceptable acid addition salt with an inorganic or organic acid such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like. The free base and a hydrochloric salt are preferred.

In certain embodiments, $R^2$ is $C_{1-12}$-alkyl, unsubstituted or substituted with one or more OH, halo, cyano or $C_{1-12}$-alkoxy. In certain embodiments, $R^2$ is $C_{1-12}$-alkyl, unsubstituted or substituted with one or more OH.

In certain embodiments, $R^2$ is unsubstituted $C_{1-12}$-alkyl.
In certain embodiments, $R^2$ is methyl.
In certain embodiments, $R^2$ is isopropyl.
In certain embodiments, $R^2$ is $C_{1-12}$-alkyl, substituted with one or more OH.
In certain embodiments, $R^2$ is 2-hydroxy-ethyl.
In certain embodiments, $R^2$ is —$(CH_2)_q$—$R^a$, wherein $R^a$ is phenyl or 5- or 6-membered heteroaryl, each unsubstituted or substituted with one or more substituents independently selected from A, and A is halo, cyano, OH, $C_{1-7}$-alkyl, halo-$C_{1-7}$-alkyl, or $C_{1-7}$-alkoxy; and q is 1, 2, 3 or 4, preferably 1.
In certain embodiments, $R^2$ is —$(CH_2)_q$—$R^a$, wherein $R^a$ is phenyl or 5- or 6-membered heteroaryl and q is 1, 2, 3 or 4, preferably 1. In certain embodiments, $R^2$ is —$CH_2$-pyridinyl or benzyl, preferably $R^2$ is —$CH_2$-pyridin-2-yl.

In certain embodiments, $R^2$ is —C(O)—$C_{1-12}$-alkyl, wherein alkyl is unsubstituted or substituted with one or more OH, halo, cyano or $C_{1-12}$-alkoxy. In certain embodiments, $R^2$ is —C(O)—$C_{1-12}$-alkyl, wherein alkyl is unsubstituted or substituted with one or more OH.

In certain embodiments, $R^2$ is —C(O)hydroxymethyl.
In certain embodiments, $R^2$ is —C(O)methyl.
In certain embodiments, $R^2$ is —C(O)($CH_2)_qOC(O)$—$C_{1-12}$-alkyl, wherein q is 1, 2, 3 or 4, preferably 1.
In certain embodiments, $R^2$ is —C(O)$CH_2OC(O)$methyl.
In certain embodiments, $R^2$ is —C(O)O—$C_{1-12}$-alkyl, wherein alkyl is unsubstituted or substituted with one or more OH, halo, cyano or $C_{1-12}$-alkoxy. In certain embodiments, $R^2$ is —C(O)O—$C_{1-12}$-alkyl.
In certain embodiments, $R^2$ is —C(O)O-t-butyl.
In certain embodiments, $R^2$ is —S(O)$_2$—$C_{1-12}$-alkyl.
In certain embodiments, $R^2$ is —S(O)$_2NR^iR^{ii}$, wherein $R^i$ and $R^{ii}$ are each independently H, $C_{1-12}$-alkyl, or together with the nitrogen atom to which they are bound form a 3- to 7-membered heterocycloalkyl containing one or two heteroatoms selected from N, O and S, which heterocycloalkyl is unsubstituted or substituted by one or more substituents independently selected from B, and B is oxo, halo, OH, $C_{1-7}$-alkyl or $C_{1-7}$-alkoxy. In certain embodiments, $R^2$ is —S(O)$_2$NR$^i$R$^{ii}$, wherein R$^i$ and R$^{ii}$ are each independently H or $C_{1-12}$-alkyl, preferably $C_{1-12}$-alkyl.

In certain embodiments, $R^2$ is —S(O)$_2$methyl.
In certain embodiments, —S(O)$_2$N(methyl)$_2$.
$R^2$ is H,
  $C_{1-12}$-alkyl, unsubstituted or substituted with one or more OH,
  —(CH$_2$)$_q$—R$^a$, wherein R$^a$ is phenyl or 5- or 6-membered heteroaryl and q is 1, 2, 3 or 4, preferably 1,
  —C(O)—$C_{1-12}$-alkyl, wherein alkyl is unsubstituted or substituted with one or more OH,
  —C(O)(CH$_2$)$_q$OC(O)—$C_{1-12}$-alkyl, wherein q is 1, 2, 3 or 4, preferably 1,
  —C(O)O—$C_{1-12}$-alkyl,
  —S(O)$_2$—$C_{1-12}$-alkyl, or
  —S(O)$_2$NR$^i$R$^{ii}$, wherein R$^i$ and R$^{ii}$ are each independently H or $C_{1-12}$-alkyl, preferably $C_{1-12}$-alkyl.
In certain embodiments, $R^3$ is Cl or F.
In a certain embodiment, $R^3$ is Cl.
In a certain embodiment, $R^3$ is F.
In a certain embodiment of the invention, the compound of formula I is provided

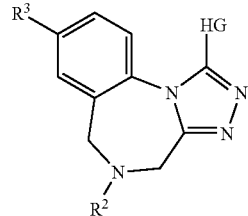

I wherein
$R^1$ is $C_{1-12}$-alkyl, unsubstituted or substituted with one or more halo, hydroxy or $C_{1-12}$-alkoxy, $C_{3-7}$-cycloalkyl,
  4-7 membered heterocycloalkyl containing one or two heteroatoms selected from O and S, preferably one O, which heterocycloalkyl is unsubstituted or substituted by one or more oxo, halo, OH, $C_{1-7}$alkyl or $C_{1-7}$alkoxy, preferably unsubstituted;
$R^2$ is H,
  $C_{1-12}$-alkyl, unsubstituted or substituted with one or more OH,
  —(CH$_2$)$_q$—R$^a$, wherein R$^a$ is phenyl or 5- or 6-membered heteroaryl and q is 1, 2, 3 or 4, preferably 1,
  —C(O)—$C_{1-12}$-alkyl, wherein alkyl is unsubstituted or substituted with one or more OH,
  —C(O)(CH$_2$)$_q$OC(O)—$C_{1-12}$-alkyl, wherein q is 1, 2, 3 or 4, preferably 1,
  —C(O)O—$C_{1-12}$-alkyl,
  —S(O)$_2$—$C_{1-12}$-alkyl, or
  —S(O)$_2$NR$^i$R$^{ii}$, wherein R$^i$ and R$^{ii}$ are each independently H or $C_{1-12}$-alkyl, preferably $C_{1-12}$-alkyl; and $R^3$ is Cl or F,
or a pharmaceutically acceptable salt thereof.

In a certain embodiment of the invention, the compound of formula I is provided as a subset of formula I'

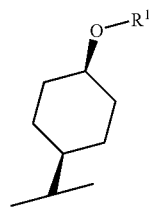

I' wherein HG is selected from

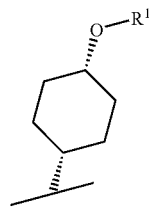

HG-1

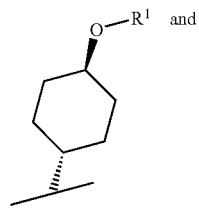

HG-2

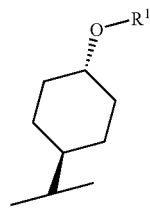

HG-3 and

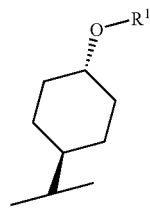

HG-4 and $R^1$, $R^2$ and $R^3$ are as described above, including all combinations thereof.

Examples for the compound according to the invention are shown in the experimental part and the table below.

TABLE 2 structures of selected examples.

| Ex. # | Structure |
|---|---|
| 1 | (4-methoxycyclohexyl)-chloro-triazolo-benzodiazepine, N-methyl |
| 2 | (4-ethoxycyclohexyl)-chloro-triazolo-benzodiazepine, N-Boc |
| 3 | (4-ethoxycyclohexyl)-chloro-triazolo-benzodiazepine, NH·HCl |
| 4 | (4-ethoxycyclohexyl)-chloro-triazolo-benzodiazepine, N-methyl |
| 5 | (4-ethoxycyclohexyl)-chloro-triazolo-benzodiazepine, N-Boc |
| 6 | (4-ethoxycyclohexyl)-chloro-triazolo-benzodiazepine, NH·HCl |
| 7 | (4-ethoxycyclohexyl)-chloro-triazolo-benzodiazepine, N-methyl |
| 8 | (4-isopropoxycyclohexyl)-chloro-triazolo-benzodiazepine, N-Boc |

TABLE 2-continued structures of selected examples.

| Ex. # | Structure |
|---|---|
| 9 | (structure) · HCl |
| 10 | (structure) |
| 11 | (structure) |
| 12 | (structure) |
| 13 | (structure) |
| 14 | (structure) |
| 15 | (structure) |
| 16 | (structure) |

TABLE 2-continued structures of selected examples.

| Ex. # | Structure |
|---|---|
| 17 | 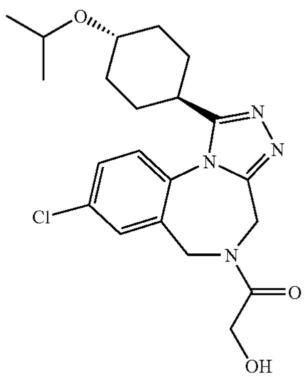 [SMILES: CC(C)O[C@H]1CC[C@H](c2nnc3n2-c2ccc(Cl)cc2CN(C(=O)CO)C3)CC1] |
| 18 | 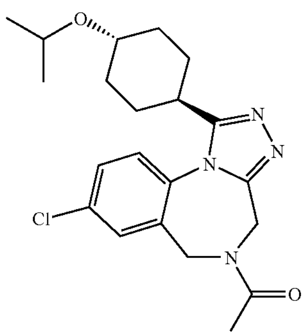 [SMILES: CC(=O)N1Cc2cc(Cl)ccc2-n2c(nnc2[C@H]2CC[C@H](OC(C)C)CC2)C1] |
| 19 | 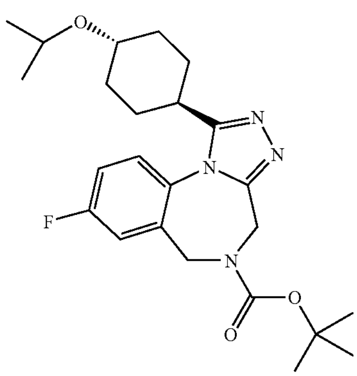 |
| 20 | 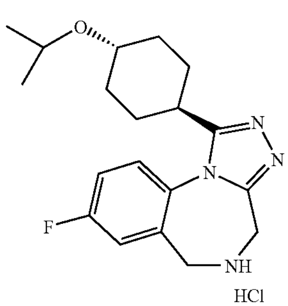 [SMILES: CC(C)O[C@H]1CC[C@H](c2nnc3n2-c2ccc(F)cc2CNC3)CC1 ; Cl] |
| 21 | |
| 22 | |
| 23 | |
| 24 | |

TABLE 2-continued structures of selected examples.

| Ex. # | Structure |
|---|---|
| 25 | *(structure)* |
| 26 | *(structure)* HCl |
| 27 | *(structure)* |
| 28 | *(structure)* |
| 29 | *(structure)* |
| 30 | *(structure)* |
| 31 | *(structure)* HCl |
| 32 | *(structure)* |

TABLE 2-continued
structures of selected examples.
| Ex. # | Structure |
|---|---|
| 33 | 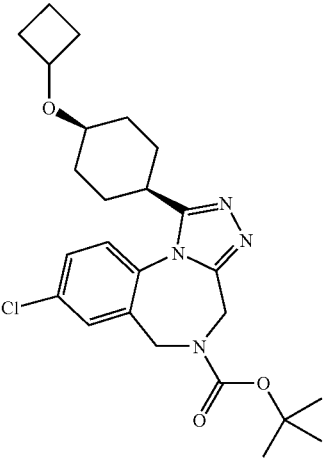 [SMILES: CC(C)(C)OC(=O)N1Cc2cc(Cl)ccc2-n2c(nnc2[C@H]2CC[C@@H](OC3CCC3)CC2)C1] |
| 34 | 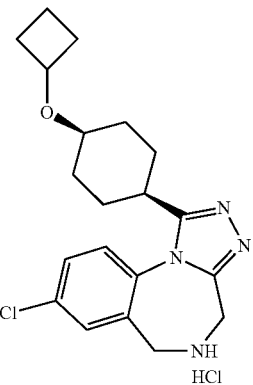 [SMILES: Clc1ccc2c(c1)CNCc1nnc([C@H]3CC[C@@H](OC4CCC4)CC3)n1-2 ; Cl] |
| 35 | 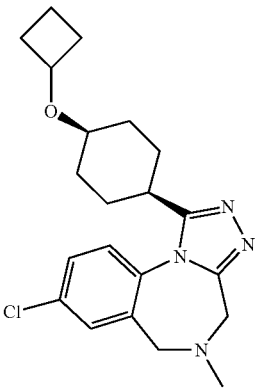 [SMILES: CN1Cc2cc(Cl)ccc2-n2c(nnc2[C@H]2CC[C@@H](OC3CCC3)CC2)C1] |
| 36 | 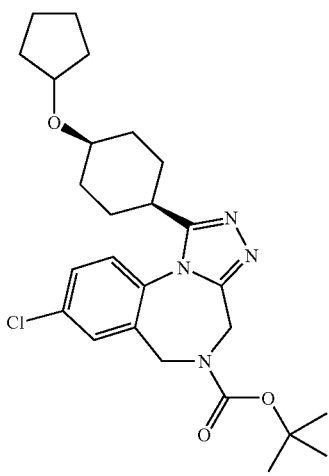 [SMILES: CC(C)(C)OC(=O)N1Cc2cc(Cl)ccc2-n2c(nnc2[C@H]2CC[C@@H](OC3CCCC3)CC2)C1] |
| 37 | 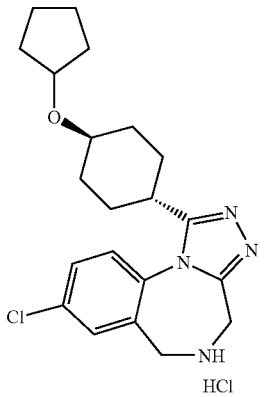 [SMILES: Clc1ccc2c(c1)CNCc1nnc([C@H]3CC[C@H](OC4CCCC4)CC3)n1-2 ; Cl] |
| 38 | 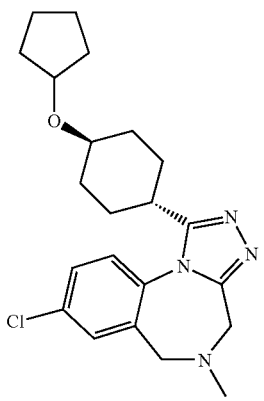 [SMILES: CN1Cc2cc(Cl)ccc2-n2c(nnc2[C@H]2CC[C@H](OC3CCCC3)CC2)C1] |

TABLE 2-continued
structures of selected examples.
| Ex. # | Structure |
|---|---|
| 39 | 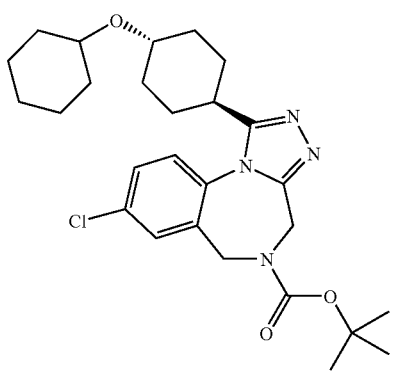 [SMILES: CC(C)(C)OC(=O)N1Cc2cc(Cl)ccc2-n2c(nnc2[C@H]2CC[C@H](OC3CCCCC3)CC2)C1] |
| 40 | 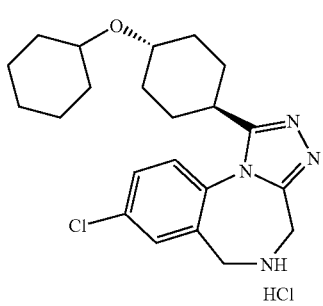 [SMILES: Clc1ccc2c(c1)CNCc1nnc([C@H]3CC[C@H](OC4CCCCC4)CC3)n1-2 ; Cl] |
| 41 | 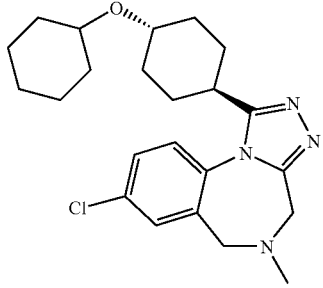 [SMILES: CN1Cc2cc(Cl)ccc2-n2c(nnc2[C@H]2CC[C@H](OC3CCCCC3)CC2)C1] |
| 42 | 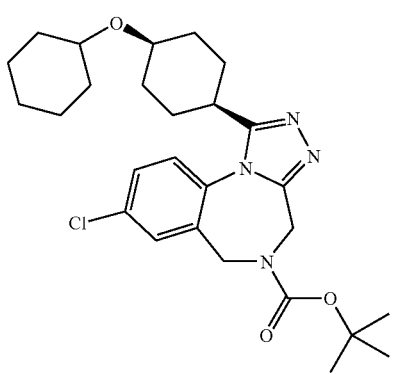 [SMILES: CC(C)(C)OC(=O)N1Cc2cc(Cl)ccc2-n2c(nnc2[C@H]2CC[C@@H](OC3CCCCC3)CC2)C1] |
| 43 | 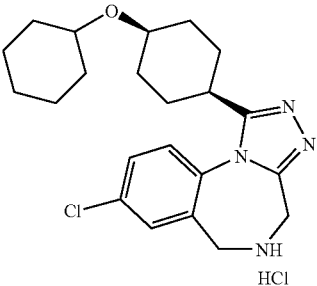 [SMILES: Clc1ccc2c(c1)CNCc1nnc([C@H]3CC[C@@H](OC4CCCCC4)CC3)n1-2 ; Cl] |
| 44 | 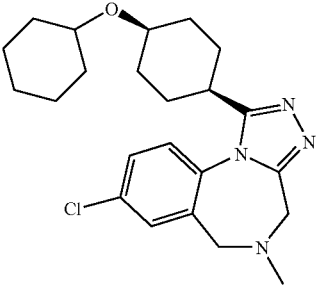 [SMILES: CN1Cc2cc(Cl)ccc2-n2c(nnc2[C@H]2CC[C@@H](OC3CCCCC3)CC2)C1] |
| 45 | 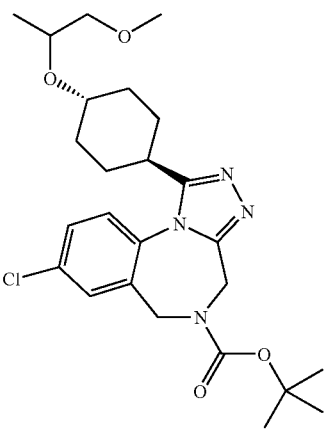 [SMILES: COCC(C)O[C@H]1CC[C@H](c2nnc3n2-c2ccc(Cl)cc2CN(C(=O)OC(C)(C)C)C3)CC1] |
| 46 | 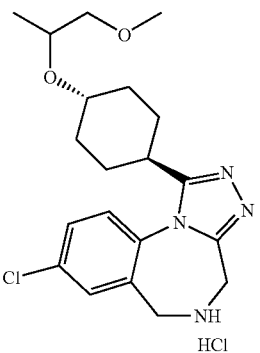 [SMILES: COCC(C)O[C@H]1CC[C@H](c2nnc3n2-c2ccc(Cl)cc2CNC3)CC1 ; Cl] |

TABLE 2-continued structures of selected examples.

| Ex. # | Structure |
|---|---|
| 47 | (structure) |
| 48 | (structure) |
| 49 | (structure) |
| 50 | (structure) |
| 51 | (structure) · HCl |
| 52 | (structure) |
| 53 | (structure) |
| 54 | (structure) |

TABLE 2-continued structures of selected examples.

| Ex. # | Structure |
|---|---|
| 55 | (structure) |
| 56 | (structure) |
| 57 | (structure) |
| 58 | (structure) |
| 59 | (structure) |
| 60 | (structure) |
| 61 | (structure) |

TABLE 2-continued structures of selected examples.

| Ex. # | Structure |
|---|---|
| 62 | (tetrahydropyran-4-yloxy-cyclohexyl triazolo-chlorobenzodiazepine, N-methyl) |
| 63 | (tetrahydropyran-4-yloxy-cyclohexyl triazolo-chlorobenzodiazepine, NH·HCl) |
| 64 | (tetrahydropyran-4-yloxy-cyclohexyl triazolo-chlorobenzodiazepine, N-methyl) |
| 65 | (trifluoromethoxy-cyclohexyl triazolo-chlorobenzodiazepine, N-Boc) |
| 66 | (trifluoromethoxy-cyclohexyl triazolo-chlorobenzodiazepine, NH·HCl) |
| 67 | (trifluoromethoxy-cyclohexyl triazolo-chlorobenzodiazepine, N-methyl) |
| 68 | (tert-butoxy-cyclohexyl triazolo-chlorobenzodiazepine, N-Boc) |
| 69 | (tert-butoxy-cyclohexyl triazolo-chlorobenzodiazepine, N-Boc) |

Preferred compounds of the invention are shown in the examples. Particularly preferred are trans-8-chloro-1-(4-ethoxy-cyclohexyl)-4H,6H-2,3,5,10b-tetraaza-benzo[e]azulene-5-carboxylic acid ten-butyl ester;
trans-8-chloro-1-(4-ethoxy-cyclohexyl)-5-methyl-5,6-dihydro-4H-2,3,5,10b-tetraaza-benzo[e]azulene;
trans-8-chloro-1-(4-isopropoxy-cyclohexyl)-4H,6H-2,3,5,10b-tetraaza-benzo[e]azulene-5-carboxylic acid tert-butyl ester;
trans-8-chloro-1-(4-isopropoxy-cyclohexyl)-5-methyl-5,6-dihydro-4H-2,3,5,10b-tetraaza-benzo[e]azulene;
trans-8-chloro-1-(4-isopropoxy-cyclohexyl)-5-methanesulfonyl-5,6-dihydro-4H-2,3,5,10b-tetraaza-benzoazulene;
trans-2-[8-chloro-1-(4-isopropoxy-cyclohexyl)-4H,6H-2,3,5,10b-tetraaza-benzoazulen-5-yl]-ethanol;
trans-8-chloro-1-(4-isopropoxy-cyclohexyl)-5-isopropyl-5,6-dihydro-4H-2,3,5,10b-tetraaza-benzoazulene;
trans-8-chloro-1-(4-isopropoxy-cyclohexyl)-4H,6H-2,3,5,10b-tetraaza-benzoazulene-5-sulfonic acid dimethylamide;
trans-8-chloro-1-(4-isopropoxy-cyclohexyl)-5-pyridin-2-yl-methyl-5,6-dihydro-4H-2,3,5,10b-tetraaza-benzoazulene;
trans-acetic acid 2-[8-chloro-1-(4-isopropoxy-cyclohexyl)-4H,6H-2,3,5,10b-tetraaza-benzoazulen-5-yl]-2-oxo-ethyl ester;
trans-1-[8-chloro-1-(4-isopropoxy-cyclohexyl)-4H,6H-2,3,5,10b-tetraaza-benzoazulen-5-yl]-2-hydroxy-ethanone;
trans-1-[8-chloro-isopropoxy-cyclohexyl)-4H,6H-2,3,5,10b-tetraaza-benzoazulen-5-yl]-ethanone;
trans-8-fluoro-1-(4-isopropoxy-cyclohexyl)-4H,6H-2,3,5,10b-tetraaza-benzo[e]azulene-5-carboxylic acid tert-butyl ester;
cis-8-chloro-1-(4-isopropoxy-cyclohexyl)-4H,6H-2,3,5,10b-tetraaza-benzo[e]azulene-5-carboxylic acid tert-butyl ester;
(RS)-trans-1-(4-sec-butoxy-cyclohexyl)-8-chloro-4H,6H-2,3,5,10b-tetraaza-benzo[e]azulene-5-carboxylic acid tert-butyl ester;
(RS)-trans-1-(4-sec-butoxy-cyclohexyl)-8-chloro-5,6-dihydro-4H-2,3,5,10b-tetraaza-benzo[e]azulene hydrochloride;
(RS)-trans-1-(4-sec-butoxy-cyclohexyl)-8-chloro-5-methyl-5,6-dihydro-4H-2,3,5,10b-tetraaza-benzo[e]azulene;
(+)-trans-1-(4-sec-butoxy-cyclohexyl)-8-chloro-5-methyl-5,6-dihydro-4H-2,3,5,10b-tetraaza-benzo[e]azulene;
(−)-trans-1-(4-sec-butoxy-cyclohexyl)-8-chloro-5-methyl-5,6-dihydro-4H-2,3,5,10b-tetraaza-benzo[e]azulene;
trans-8-chloro-1-(4-cyclobutoxy-cyclohexyl)-4H,6H-2,3,5,10b-tetraaza-benzo[e]azulene-5-carboxylic acid tert-butyl ester;
trans-8-chloro-1-(4-cyclobutoxy-cyclohexyl)-5,6-dihydro-4H-2,3,5,10b-tetraaza-benzo[c]azulene hydrochloride;
trans-8-chloro-1-(4-cyclobutoxy-cyclohexyl)-5-methyl-5,6-dihydro-4H-2,3,5,10b-tetraaza-benzo[e]azulene;
cis-8-chloro-1-(4-cyclobutoxy-cyclohexyl)-4H,6H-2,3,5,10b-tetraaza-benzo[e]azulene-5-carboxylic acid tert-butyl ester;
cis-8-chloro-1-(4-cyclobutoxy-cyclohexyl)-5-methyl-5,6-dihydro-4H-2,3,5,10b-tetraaza-benzo[e]azulene;
trans-8-chloro-1-(4-cyclopentyloxy-cyclohexyl)-4H,6H-2,3,5,10b-tetraaza-benzo[e]azulene-5-carboxylic acid tert-butyl ester;
trans-8-chloro-1-(4-cyclopentyloxy-cyclohexyl)-5,6-dihydro-4H-2,3,5,10b-tetraaza-benzo[e]azulene hydrochloride;
trans-8-chloro-1-(4-cyclopentyloxy-cyclohexyl)-5-methyl-5,6-dihydro-4H-2,3,5,10b-tetraaza-benzo[e]azulene;
trans-8-chloro-1-(4-cyclohexyloxy-cyclohexyl)-4H,6H-2,3,5,10b-tetraaza-benzoazulene-5-carboxylic acid tert-butyl ester;
trans-8-chloro-1-(4-cyclohexyloxy-cyclohexyl)-5-methyl-5,6-dihydro-4H-2,3,5,10b-tetraaza-benzoazulene;
(RS)-trans-8-chloro-1-[4-(2-methoxy-1-methyl-ethoxy)-cyclohexyl]-4H,6H-2,3,5,10b-tetraaza-benzo[e]azulene-5-carboxylic acid tert-butyl ester;
(RS)-trans-8-chloro-1-[4-(2-methoxy-1-methyl-ethoxy)-cyclohexyl]-5-methyl-5,6-dihydro-4H-2,3,5,10b-tetraaza-benzo[e]azulene;
(−)-trans-8-chloro-1-[4-(2-methoxy-1-methyl-ethoxy)-cyclohexyl]-5-methyl-5,6-dihydro-4H-2,3,5,10b-tetraaza-benzo[e]azulene;
(RS)-trans-8-chloro-1-[4-(2-hydroxy-1-methyl-ethoxy)-cyclohexyl]-4H,6H-2,3,5,10b-tetraaza-benzo[e]azulene-5-carboxylic acid tert-butyl ester;
(RS)-trans-8-chloro-1-[4-(2-fluoro-1-methyl-ethoxy)-cyclohexyl]-5-methyl-5,6-dihydro-4H-2,3,5,10b-tetraaza-benzo[e]azulene;
(RS)-trans-8-chloro-1-[4-(3,3,3-trifluoro-1-methyl-propoxy)-cyclohexyl]-4H,6H-2,3,5,10b-tetraaza-benzo[e]azulene-5-carboxylic acid tert-butyl ester;
(RS)-trans-8-chloro-5-methyl-1-[4-(3,3,3-trifluoro-1-methyl-propoxy)-cyclohexyl]-5,6-dihydro-4H-2,3,5,10b-tetraaza-benzo[e]azulene;
trans-8-chloro-1-[4-(oxetan-3-yloxy)-cyclohexyl]-4H,6H-2,3,5,10b-tetraaza-benzo[e]azulene-5-carboxylic acid tert-butyl ester;
trans-8-chloro-1-[4-(tetrahydro-pyran-4-yloxy)-cyclohexyl]-4H,6H-2,3,5,10b-tetraaza-benzoazulene-5-carboxylic acid tert-butyl ester;
cis-8-chloro-1-[4-(tetrahydro-pyran-4-yloxy)-cyclohexyl]-4H,6H-2,3,5,10b-tetraaza-benzoazulene-5-carboxylic acid tert-butyl ester, and
trans-1-(4-tert-butoxy-cyclohexyl)-8-chloro-4H,6H-2,3,5,10b-tetraaza-benzo[e]azulene-5-carboxylic acid tert-butyl ester.

Particularly preferred are trans-8-chloro-1-(4-isopropoxy-cyclohexyl)-5-methyl-5,6-dihydro-4H-2,3,5,10b-tetraaza-benzo[e]azulene, trans-8-chloro-1-(4-cyclobutoxy-cyclohexyl)-5-methyl-5,6-dihydro-4H-2,3,5,10b-tetraaza-benzo[e]azulene, and trans-8-chloro-1-(4-cyclopentyloxy-cyclohexyl)-5-methyl-5,6-dihydro-4H-2,3,5,10b-tetraaza-benzo[e]azulene.

Most preferred is trans-8-chloro-1-(4-cyclopentyloxy-cyclohexyl)-5-methyl-5,6-dihydro-4H-2,3,5,10b-tetraaza-benzo[e]azulene.

A certain embodiment of the invention is a compound as described in any of the embodiments obtainable by a process as described herewithin.

A certain embodiment of the invention is a compound as described in any of the embodiments for the use as therapeutically active substance.

A certain embodiment of the invention is a compound as described in any of the embodiments for a use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a pharmaceutical composition comprising a compound as described in any of the embodiments.

A certain embodiment of the invention is the use of a compound as described in any of the embodiments for the preparation of a medicament.

A certain embodiment of the invention is the use of a compound as described in any of the embodiments for the preparation of a medicament, wherein the medicament is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a method for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior which comprises administering a therapeutically effective amount of a compound of formula I.

In a certain embodiment, the compounds of formula (I) of the invention can be manufactured according to a process comprising the step of reacting a compound of formula (II)

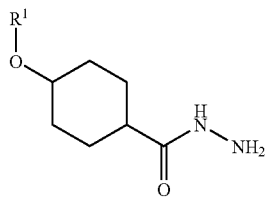

II with a compound of formula (III)

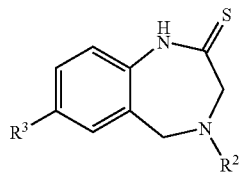

III to obtain a compound of formula (I) wherein $R^1$, $R^2$ and $R^3$ are as defined hereinabove for formula (I).

The processes are described in more detail with the following general schemes and procedures A to I.

Scheme 1: General Scheme A

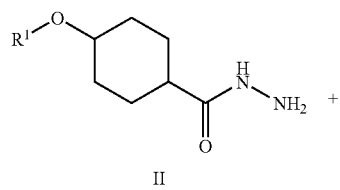

II

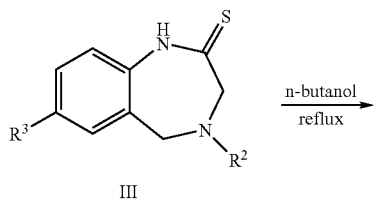

III

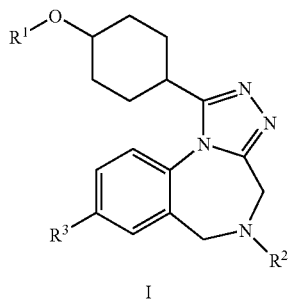

I

Compounds of formula (I) can be prepared by thermal condensation of a hydrazide derivative of formula (II) and a thiolactam derivative of formula (III). The synthesis of compounds of formula (II) is outlined in general schemes D-I hereinafter. Compounds of formula (III) can be prepared following the general scheme C as described hereinafter. General scheme A is hereinafter further illustrated with general procedure IV.

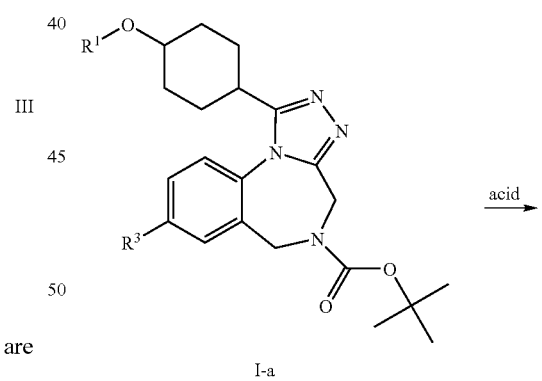

I-a

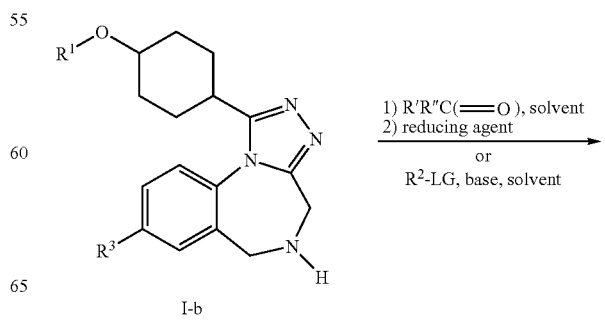

I-b

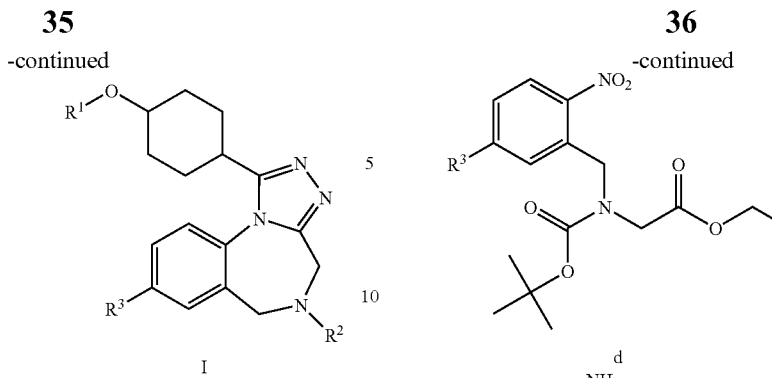

Scheme 2: General Scheme B Compounds of formula (I) with $R^2$ different from H can be prepared from compounds of formula (I-b) (compounds of formula (I) wherein $R^2$ is H) according to methods known in the art, e.g. by treating a compound of formula (I-b) with an inorganic base such as a carbonate salt or an organic base such as a tertiary amine and an electrophilic reactant $R^2$-LG (wherein LG is a leaving group, e.g. halogen or sulfonyl) which is either commercially available or easily prepared according to methods and starting materials well known in the art. Alternatively, compounds of formula (I) can be obtained via reductive alkylation by consecutively treating a compound of formula (I-b) with a ketone or aldehyde and a suitable reducing agent, e.g. a borohydride derivative such as sodium borohydride, sodium cyanoborohydride or sodium triacetoxyborohydride. Compounds of formula (I-b) can be obtained by cleavage of the substituent $R^2$ of compound of formula I using methods known in the art. Compounds of formula (I-b) are conveniently obtained as the salt or the free base after basic aqueous work-up by treatment of compounds of formula (I-a) (compounds of formula (I) in which $R^2$ is tort-butoxycarbonyl) with an acid in a suitable solvent, e.g. methanesulfonic acid in dichloromethane or tetrahydrofuran or hydrochloric acid in methanol. General scheme B is hereinafter further illustrated with general procedures V and VI.

Scheme 3: General Scheme C

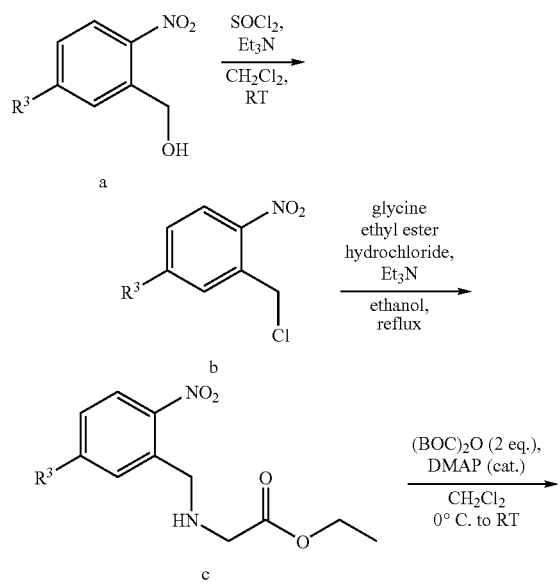

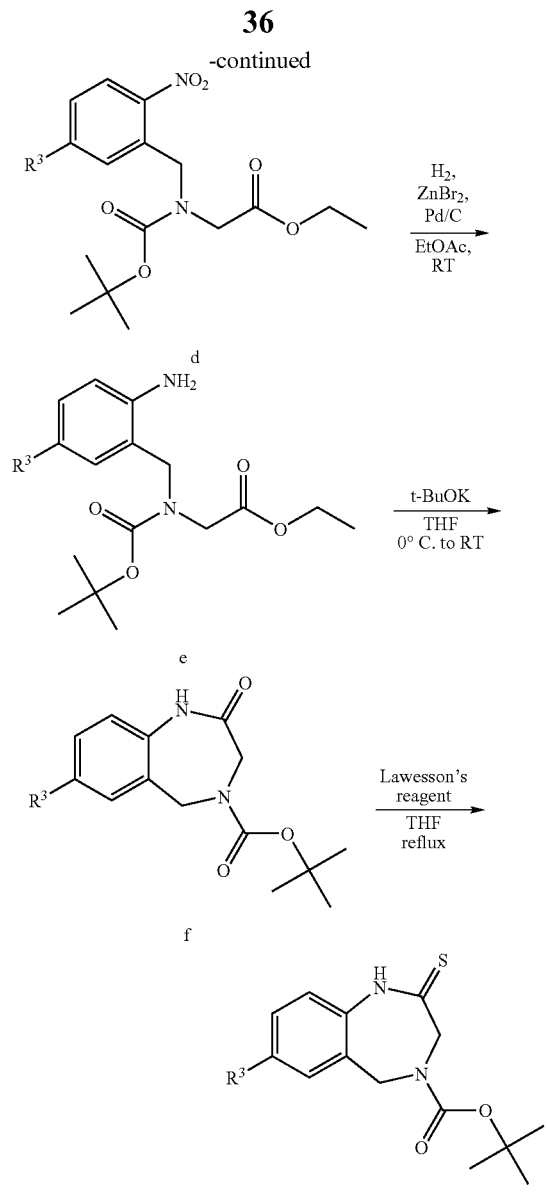

Thiolactams of formula (III-1) (compounds of formula (III) in which $R^2$ is tert-butoxycarbonyl) can be obtained as follows: Transformation of a 2-nitrobenzyl alcohol of formula (a) to a benzylic chloride of formula (b) can be effected by a chlorinating reagent such as thionyl chloride in the presence of an organic tertiary amine base. Alkylation of a compound of formula (b) with glycine ethyl ester hydrochloride in the presence of an organic tertiary amine base and N-protection of the resulting compound of formula (c) using di-tert-butyl dicarbonate and a catalytic amount of 4-N,N-dimethylaminopyridine gives compounds of formula (d). The nitro group can be reduced selectively by hydrogenation over palladium on charcoal, which has been pretreated with a zinc halide such as zinc bromide, to give aniline intermediates of formula (e). Cyclization to lactams of formula (f) is achieved by treatment of compounds of formula (e) with a suitable base, e.g. potassium tert-butoxide, in tetrahydrofuran. A thiolactam derivative of formula (III-1) is obtained by treatment of a compound of formula (f) with Lawesson's reagent (2,4-bis-(4-methoxyphenyl)-1,3,2,4-dithiadiphosphetane-2,4-disulfide) or phosphorous pentasulfide at elevated temperature.

Scheme 4: General Scheme D

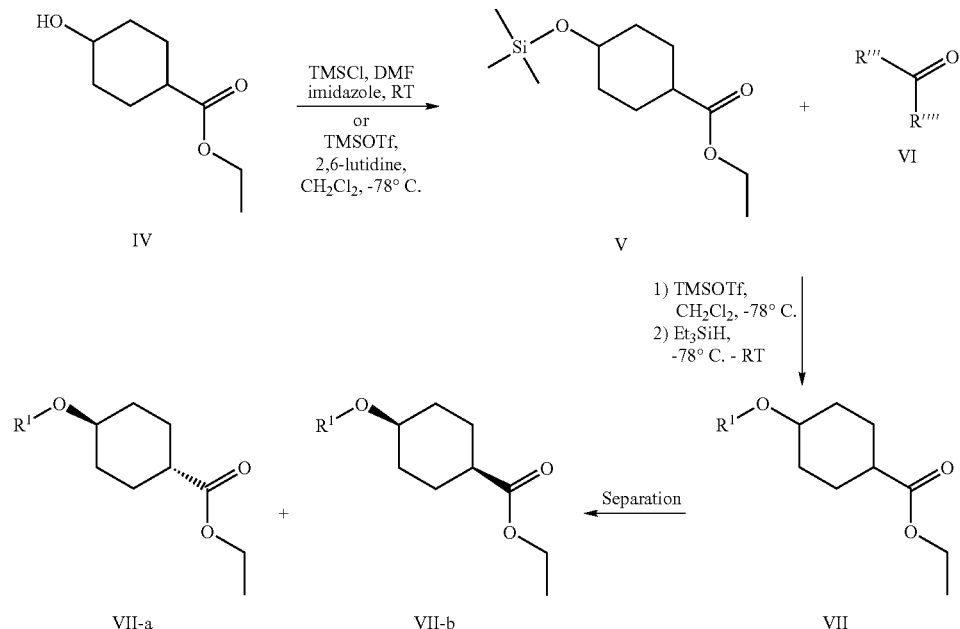

4-Alkoxy-cyclohexanecarboxylic acid esters of formula (VII) can be obtained by reductive etherification as follows: 4-Hydroxy-cyclohexanecarboxylic acid ethyl ester (IV) is converted to 4-trimethylsilanyloxy-cyclohexanecarboxylic acid ethyl ester (V) by O-silylation methods known in the art, e.g. by treatment with a silylating agent such as trimethylsilyl chloride or trimethylsilyl triflate in the presence of a base such as imidazole or 2,6-lutidine in a suitable solvent such as N,N-dimethylformamide or dichloromethane. Consecutive treatment of 4-trimethylsilanyloxy-cyclohexanecarboxylic acid ethyl ester (V) and a ketone or aldehyde of formula (VI) with trimethylsilyl triflate in dichloromethane and a reducing agent such as triethylsilane leads to 4-alkoxy-cyclohexanecarboxylic acid esters of formula (VII). Compounds of formula (VII) are usually obtained as a mixture of cis- and trans-isomers, which can in some cases be separated chromatographically to give the pure trans-4-alkoxy-cyclohexanecarboxylic acid ester of formula (VII-a) and cis-4-alkoxy-cyclohexanecarboxylic acid ester of formula (VII-b). General scheme D is hereinafter further illustrated by general procedure I.

Scheme 5: General Scheme E

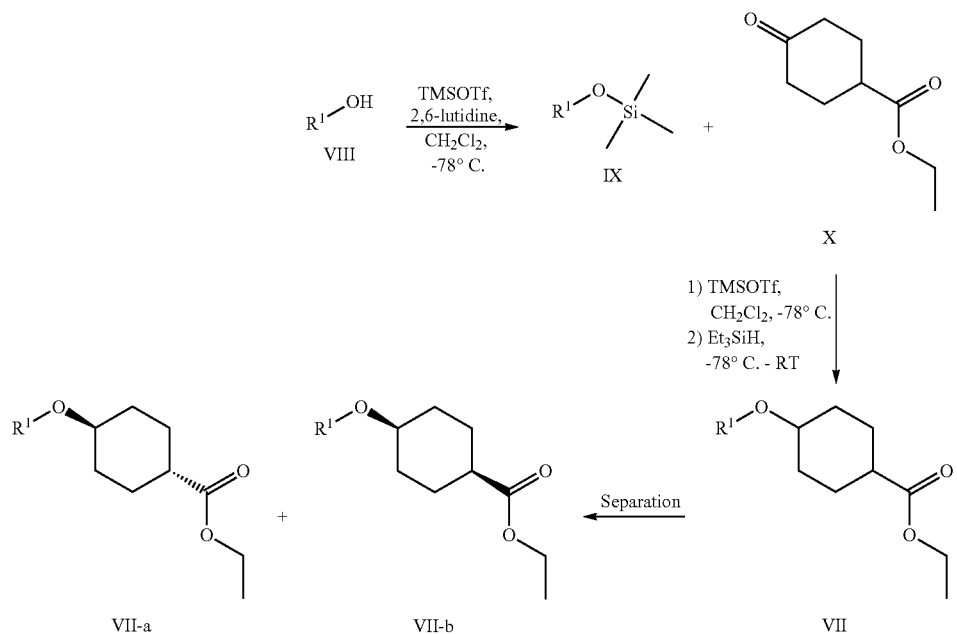

Alternatively, 4-alkoxy-cyclohexanecarboxylic acid esters of formula (VII) can be obtained by reductive etherification as follows: Consecutive treatment of an alkoxy-trimethyl-silane of formula (IX) and 4-cyclohexanonecarboxylic acid ethyl ester (X) with trimethylsilyl triflate in dichloromethane and a reducing agent such as triethylsilane gives 4-alkoxy-cyclohexanecarboxylic acid esters of formula (VII). Compounds of formula (VII) are usually obtained as a mixture of cis- and trans-isomers, which can in some cases be separated chromatographically to give the pure trans-4-alkoxy-cyclohexanecarboxylic acid ester of formula (VII-a) and cis-4-alkoxy-cyclohexanecarboxylic acid ester of formula (VII-b). Alkoxy-trimethyl-silanes of formula (IX) are either commercially available or are prepared using O-silylation methods known in the art, e.g. by treating an alcohol of general formula (VIII) with a silylating agent such as trimethylsilyl chloride or trimethylsilyl triflate in the presence of a base such as imidazole or 2,6-lutidine in a suitable solvent such as N,N-dimethylformamide or dichloromethane. Alternatively, alkoxy-trimethyl-silanes of formula (IX) can be prepared in situ without isolation prior to the reductive etherification step with 4-cyclohexanonecarboxylic acid ethyl ester (X) by treating an alcohol of general formula (VIII) with trimethylsilyl triflate and 2,6-lutidine in dichloromethane. General scheme E is hereinafter further illustrated by general procedures IIA and IIB.

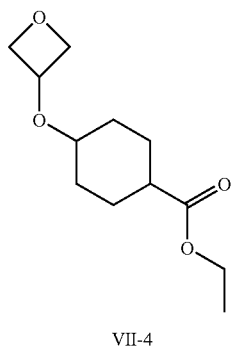

VII-4

An oxetan-3-yloxy compound of formula (VII-4) can be obtained by treatment of the compound of formula (VII-3) with potassium tert-butoxide in toluene at reflux. The compound of formula (VII-3) is formed by monotosylation of the dihydroxy derivative of formula (VII-2), which is prepared by hydrogenolytic double-O-debenzylation of the compound of formula (VII-1). The compound of formula (VII-1) can be obtained from 1,3-dibenzyloxy-2-propanol according to the reductive etherification procedure described in general scheme E.

Scheme 6: General Scheme F

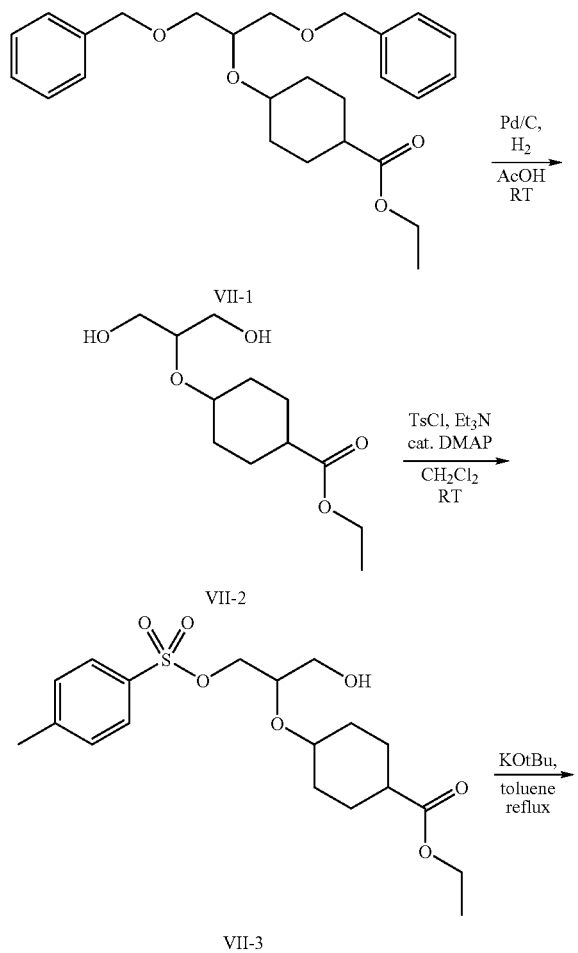

Scheme 7: General Scheme G

4-Trifluoromethox-cyclohexanecarboxcylic acid ethyl ester (VII-5) can be prepared by treatment of intermediate (XI) with N-bromosuccinimide and HF-pyridine in dichloromethane. Compound (XI) is obtained by O-deprotonation of 4-hydroxy-cyclohexanecarboxylic acid ethyl ester with sodium hydride followed by sequential addition of carbon disulfide and methyl iodide.

Scheme 8: General Scheme H

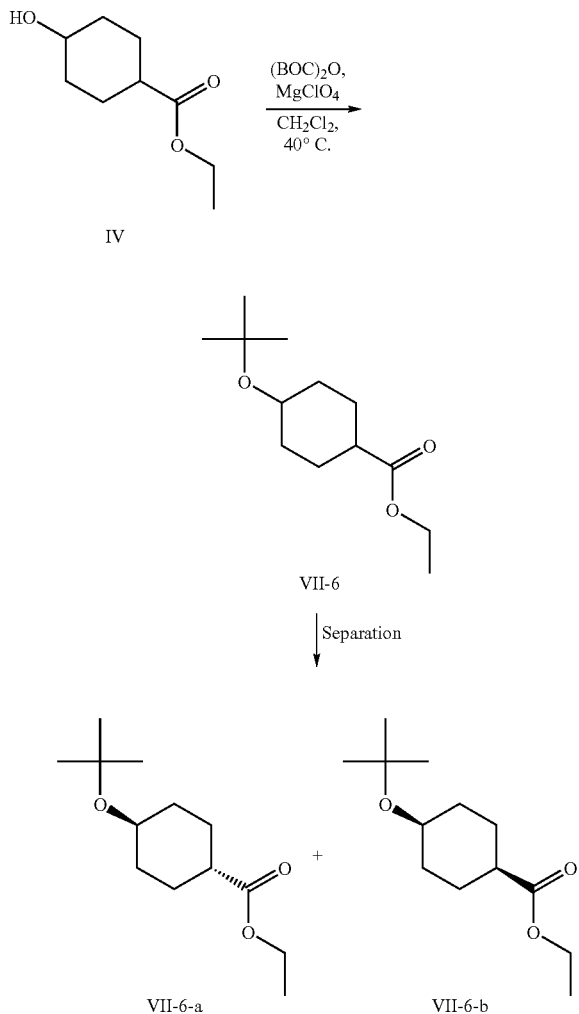

Cis/trans-4-tert-Butoxy-cyclohexanecarboxylic acid ethyl ester (VII-6) can be prepared by treating cis/trans-4-hydroxy-cyclohexanecarboxylic acid ethyl ester (IV) with di-tert-butyl dicarbonate in the presence of magnesium chloride. The pure trans isomer (VII-6-a) and the pure cis isomer (VII-6-b) can be obtained by chromatographic separation.

Scheme 9: General Scheme I

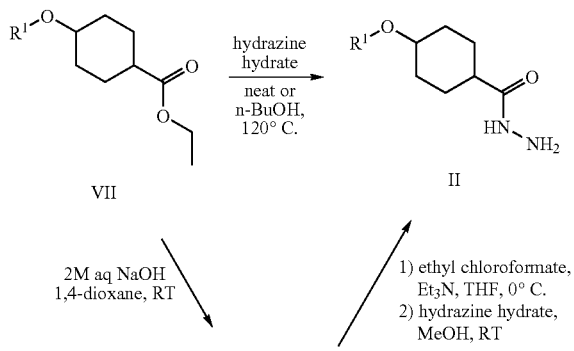

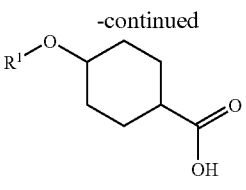

A 4-aryloxy-cyclohexanecarboxylic acid ester of formula (VII) can be converted to a hydrazide derivative of formula (II) by heating with hydrazine hydrate. Alternatively, an ester derivative of formula (VII) can be hydrolyzed to a carboxylic acid derivative of formula (XII) using a biphasic mixture of aqueous sodium or potassium hydroxide solution and an etheral solvent such as dioxan. A hydrazide derivative of formula (II) can be obtained by activating an acid intermediate of formula (XII), e.g. with ethyl chloroformate, thionyl chloride, oxalylchloride or a peptide coupling reagent, and subsequent coupling with hydrazine. General scheme I is hereinafter further illustrated by general procedures IIIA and IIIB.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can derivatized at functional groups to provide derivatives which are capable of conversion back to the parent compound in vivo.

Pharmacological Tests

The compounds of the present invention exhibit V1a activity, They are selective inhibitors of the V1a receptor and are therefore likely to have a low potential to cause unwanted off-target related side-effects. The V1a activity can be detected as described below.

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM magnesium dichloride adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM sodium chloride, 5 mM potassium chloride, 2 mM Calcium dichloride, 10 mM magnesium dichloride) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% dimethyl sulfoxide. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

The following representative data show the antagonistic activity against human V1a receptor of compounds according to present invention.

TABLE 3 human V1a pKi of selected examples

| Ex. # | pKi (hV1a) |
|---|---|
| 1 | 7.03 |
| 2 | 8.62 |
| 3 | 7.20 |
| 4 | 8.17 |
| 5 | 7.85 |
| 6 | 6.05 |
| 7 | 7.26 |
| 8 | 8.89 |
| 9 | 7.76 |
| 10 | 8.55 |
| 11 | 8.96 |
| 12 | 8.64 |
| 13 | 8.82 |
| 14 | 9.00 |
| 15 | 8.85 |
| 16 | 8.46 |
| 17 | 8.46 |
| 18 | 8.60 |
| 19 | 8.42 |
| 20 | 6.60 |
| 21 | 7.53 |
| 22 | 8.05 |
| 23 | 6.44 |
| 24 | 7.57 |
| 25 | 8.43 |
| 26 | 7.90 |
| 27 | 8.68 |
| 28 | 8.80 |
| 29 | 8.80 |
| 30 | 8.55 |
| 31 | 7.97 |
| 32 | 8.89 |
| 33 | 8.12 |
| 34 | 6.84 |
| 35 | 8.10 |
| 36 | 8.49 |
| 37 | 8.46 |
| 38 | 9.10 |
| 39 | 8.19 |
| 40 | 7.46 |
| 41 | 8.54 |
| 42 | 7.75 |
| 43 | 6.76 |
| 44 | 7.85 |
| 45 | 8.43 |
| 46 | 6.93 |
| 47 | 7.95 |
| 48 | 7.32 |
| 49 | 8.26 |
| 50 | 8.57 |
| 51 | 6.73 |
| 52 | 7.72 |
| 53 | 8.55 |
| 54 | 8.07 |
| 55 | 7.12 |
| 56 | 8.17 |
| 57 | 8.21 |
| 58 | 7.33 |
| 59 | 8.25 |
| 60 | 8.15 |
| 61 | 6.35 |
| 62 | 7.70 |
| 63 | 6.54 |
| 64 | 7.77 |
| 65 | 7.84 |
| 66 | 6.71 |
| 67 | 7.58 |
| 68 | 8.42 |

Pharmaceutical Compositions

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

Examples of compositions according to the invention are, but are not limited to:

EXAMPLE A

Tablets of the following composition are manufactured in the usual manner:

TABLE 4 possible tablet composition

| ingredient | mg/tablet | | | |
|---|---|---|---|---|
| | 5 | 25 | 100 | 500 |
| 1. Compound of formula I | 5 | 25 | 100 | 500 |
| 2. Lactose | 45 | 105 | 30 | 150 |
| 3. Corn Starch | 15 | 6 | 6 | 60 |
| 4. Microcrystalline Cellulose | 34 | 30 | 30 | 450 |
| 5. Magnesium Stearate | 1 | 1 | 1 | 1 |
| Total | 100 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 5 possible capsule ingredient composition

| ingredient | mg/capsule | | | | |
|---|---|---|---|---|---|
| | 5 | 10 | 25 | 100 | 500 |
| 1. Compound of formula I | 5 | 10 | 25 | 100 | 500 |
| 2. Lactose | 159 | 155 | 123 | 148 | — |
| 3. Corn Starch | 25 | 30 | 35 | 40 | 70 |
| 4. Talc | 10 | 5 | 15 | 10 | 25 |
| 5. Magnesium Stearate | 1 | — | 2 | 2 | 5 |
| Total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatine capsules.

EXAMPLE B-2

Soft Gelatine Capsules of the following composition are manufactured:

TABLE 6 possible soft gelatine capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 7 possible soft gelatine capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure
The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 8 possible suppository composition

| ingredient | mg/supp. |
|---|---|
| Compound of formula I | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, the suppositories are then removed from the moulds and packed individually in wax paper or metal foil.

EXAMPLE D

Injection solutions of the following composition are manufactured:

TABLE 9

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 10

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesiumstearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

EXAMPLES

The following examples 1-69 are provided for illustration of the invention. They should not be considered as limiting the scope of the invention, but merely as being representative thereof.

Intermediate of Formula (V)

cis/trans-4-Trimethylsilanyloxy-cyclohexanecarboxylic acid ethyl ester (2:1)

To a solution of cis/trans-4-hydroxycyclohexane carboxylic acid ethyl ester (2:1) (5.0 g, 29 mmol) and imidazole (4.4 g, 64 mmol) in N,N-dimethylformamide (90 ml) was added trimethylsilyl chloride (4.0 ml, 32 mmol) at 0-5° C. Stirring for 1 h at room temperature was followed by partitioning between tert-butyl methyl ether (300 ml) and water (150 ml). The layers were separated. The organic layer was washed with two 150-ml portions of water and one 50-ml portion of brine, dried over anhydrous sodium sulfate and concentrated in vacuo to give the title compound (6.7 g, 94%) as colorless oil. MS m/e: 245 (M+H$^+$).

4-Alkoxy-cyclohexanecarboxylic acid ester intermediates of formula (VII) Reductive Etherification General Procedure I:

To a solution of cis/trans-4-trimethylsilanyloxy-cyclohexanecarboxylic acid ethyl ester (2:1) in dichloromethane (0.1 M) are added consecutively a ketone or an aldehyde of formula (VI) (0.85 eq) and trimethylsilyl trifluoromethanesulfonate (0.10 eq) at −78° C. The reaction mixture is stirred for 1 h. After addition of triethylsilane (1 eq) the cooling bath is removed and the reaction mixture is allowed to warm to room temperature. Stirring is continued over night. The mixture is quenched with saturated aqueous sodium bicarbonate solution. The layers are separated. The organic layer is dried over anhydrous sodium sulfate and concentrated in vacuo. Purification by flash-chromatography gives a 4-alkoxy-cyclohexanecarboxylic acid ester intermediate of formula (VII).

General Procedure IIA:

An alkoxy-trimethyl-silane intermediate of formula (IX) is formed in situ by adding trimethylsilyl trifluoromethanesulfonate (1 eq) to a solution of an alcohol derivative of formula (VIII) (1 eq) and 2,6-lutidine (1 eq) in dichloromethane (0.1 M) at −78° C. After 1 h 4-cyclohexanonecarboxylic acid ethyl ester (X) (0.85 eq) and trimethylsilyl trifluoromethanesulfonate (0.1 eq) are added consecutively. The reaction mixture is stirred for 1 h. After addition of triethylsilane (2 eq) the cooling bath is removed and the reaction mixture is allowed to warm to room temperature. Stirring is continued over night. The mixture is quenched with saturated aqueous sodium bicarbonate solution. The layers are separated. The organic layer is dried over anhydrous sodium sulfate and concentrated in vacuo. Purification by flash-chromatography gives a 4-alkoxy-cyclohexanecarboxylic acid ester intermediate of formula (VII).

General Procedure IIB:

A trimethylsilyloxy intermediate of formula (IX), which is commercially available or which can be prepared according to methods known in the art, is dissolved in dichloromethane (0.1 M). 4-Cyclohexanonecarboxylic acid ethyl ester (X) (0.85 eq) and trimethylsilyl trifluoro-methanesulfonate (0.1 eq) are added consecutively at −78° C. The reaction mixture is stirred for 1 h. After addition of triethylsilane (2 eq) the cooling bath is removed and the reaction mixture is allowed to warm to room temperature. Stirring is continued over night. The mixture is quenched with saturated aqueous sodium bicarbonate solution. The layers are separated. The organic layer is dried over anhydrous sodium sulfate and concentrated in vacuo. Purification by flash-chromatography gives a 4-alkoxy-cyclohexanecarboxylic acid ester intermediate of formula (VII).

4-Alkoxy-cyclohexanecarboxylic acid ester 1 trans-4-Ethoxy-cyclohexanecarboxylic acid ethyl ester and

4-Alkoxy-cyclohexanecarboxylic acid ester 2 cis-4-Ethoxy-cyclohexanecarboxylic acid ethyl ester trans-4-Ethoxy-cyclohexanecarboxylic acid ethyl ester and cis-4-ethoxy-cyclohexanecarboxylic acid ethyl ester were obtained from acetaldehyde according to general procedure I after separation by flash-column chromatography.

trans-4-Ethoxy-cyclohexanecarboxylic acid ethyl ester was obtained as light yellow oil in 18% yield. MS m/e: 200 (M$^+$)

cis-4-Ethoxy-cyclohexanecarboxylic acid ethyl ester was obtained as light yellow oil in 24% yield. MS m/e: 201 (M+H$^+$)

4-Alkoxy-cyclohexanecarboxylic acid ester 3 trans-4-Isopropoxy-cyclohexanecarboxylic acid ethyl ester and

4-Alkoxy-cyclohexanecarboxylic acid ester 4 cis-4-Isopropoxy-cyclohexanecarboxylic acid ethyl ester trans-4-Isopropoxy-cyclohexanecarboxylic acid ethyl ester and cis-4-isopropoxy-cyclohexanecarboxylic acid ethyl ester were obtained from acetone according to general procedure I after separation by flash-column chromatography.

trans-4-Isopropoxy-cyclohexanecarboxylic acid ethyl ester was obtained as colorless oil in 23% yield. MS m/e: 214 (M$^+$)

cis-4-Isopropoxy-cyclohexanecarboxylic acid ethyl ester was obtained as light yellow oil in 57% yield. MS m/e: 215 (M+H$^+$)

4-Alkoxy-cyclohexanecarboxylic acid ester 5 trans-4-sec-Butoxy-cyclohexanecarboxylic acid ethyl ester and

4-Alkoxy-cyclohexanecarboxylic acid ester 6 cis-4-sec-Butoxy-cyclohexanecarboxylic acid ethyl ester trans-4-sec-Butoxy-cyclohexanecarboxylic acid ethyl ester and cis-4-sec-Butoxy-cyclohexanecarboxylic acid ethyl ester were obtained from 2-butanone according to general procedure I after separation by flash-column chromatography.

trans-4-sec-Butoxy-cyclohexanecarboxylic acid ethyl ester was obtained as colorless oil in 22% yield. MS (EI) m/e: 228 (M$^+$, 1%), 199 ([M-C$_2$H$_5$]$^+$, 6%), 155 ([M-C$_4$H$_9$O]$^+$, 100%)

cis-4-sec-Butoxy-cyclohexanecarboxylic acid ethyl ester was obtained as light yellow oil in 37% yield. MS m/e: 229 (M+H$^+$)

4-Alkoxy-cyclohexanecarboxylic acid ester 7 trans-4-Cyclobutoxy-cyclohexanecarboxylic acid ethyl ester and

4-Alkoxy-cyclohexanecarboxylic acid ester 8 cis-4-Cyclobutoxy-cyclohexanecarboxylic acid ethyl ester trans-4-Cyclobutoxy-cyclohexanecarboxylic acid ethyl ester and cis-4-cyclobutoxy-cyclohexanecarboxylic acid ethyl ester were obtained from cyclobutanone according to general procedure I after separation by flash-column chromatography.

trans-4-Cyclobutoxy-cyclohexanecarboxylic acid ethyl ester was obtained as colorless oil in 19% yield. MS (EI) m/e: 155 ([M-C$_4$H$_7$O]$^+$, 49%)

cis-4-Cyclobutoxy-cyclohexanecarboxylic acid ethyl ester was obtained as light yellow oil in 58% yield. MS m/e: 227 (M+H$^+$)

4-Alkoxy-cyclohexanecarboxylic acid ester 9 trans-4-Cyclopentyloxy-cyclohexanecarboxylic acid ethyl ester and

4-Alkoxy-cyclohexanecarboxylic acid ester 10 cis-4-Cyclopentyloxy-cyclohexanecarboxylic acid ethyl ester trans-4-Cyclopentoxy-cyclohexanecarboxylic acid ethyl ester and cis-4-cyclopentoxy-cyclohexanecarboxylic acid ethyl ester were obtained from cyclopentanone according to general procedure I after separation by flash-column chromatography.

trans-4-Cyclopentoxy-cyclohexanecarboxylic acid ethyl ester was obtained as colorless oil in 8% yield. MS (EI) m/e: 240 (M$^{+\cdot}$ 1%), 155 [M-C$_5$H$_9$O]$^+$, 30%)

cis-4-Cyclopentoxy-cyclohexanecarboxylic acid ethyl ester was obtained as colorless oil in 29% yield. MS m/e: 241 (M+H$^+$)

4-Alkoxy-cyclohexanecarboxylic acid ester 11 trans-4-Cyclohexyloxy-cyclohexanecarboxylic acid ethyl ester and

4-Alkoxy-cyclohexanecarboxylic acid ester 12 cis-4-Cyclohexyloxy-cyclohexanecarboxylic acid ethyl ester trans-4-Cyclopentoxy-cyclohexanecarboxylic acid ethyl ester and cis-4-cyclopentoxy-cyclohexanecarboxylic acid ethyl ester were obtained from cyclohexanone according to general procedure I after separation by flash-column chromatography.

trans-4-Cyclohexyloxy-cyclohexanecarboxylic acid ethyl ester was obtained as colorless oil in 15% yield. MS (EI) m/e: 254 (M$^+$)

cis-4-Cyclohexyloxy-cyclohexanecarboxylic acid ethyl ester was obtained as colorless oil in 51% yield. MS m/e: 255 (M+H$^+$)

4-Alkoxy-cyclohexanecarboxylic acid ester 13

(RS)-trans-4-(2-Methoxy-1-methyl-ethoxy)-cyclohexanecarboxylic acid ethyl ester and 4-Alkoxy-cyclohexanecarboxylic acid ester 14

(RS)-cis-4-(2-Methoxy-1-methyl-ethoxy)-cyclohexanecarboxylic acid ethyl ester (RS)-trans-4-(2-Methoxy-1-methyl-ethoxy)-cyclohexanecarboxylic acid ethyl ester and (RS)-cis-4-(2-methoxy-1-methyl-ethoxy)-cyclohexanecarboxylic acid ethyl ester were obtained from methoxyacetone according to general procedure I after separation by flash-column chromatography.

(RS)-trans-4-(2-Methoxy-1-methyl-ethoxy)-cyclohexanecarboxylic acid ethyl ester was obtained as colorless oil in 21% yield. MS m/e: 245 (M+H⁺)

(RS)-cis-4-(2-Methoxy-1-methyl-ethoxy)-cyclohexanecarboxylic acid ethyl ester was obtained as colorless oil in 43% yield. MS m/e: 245 (M+H⁺)

4-Alkoxy-cyclohexanecarboxylic acid ester 15

(RS)-trans-4-(2-Acetoxy-1-methyl-ethoxy)-cyclohexanecarboxylic acid ethyl ester and 4-Alkoxy-cyclohexanecarboxylic acid ester 16

(RS)-cis-4-(2-Acetoxy-1-methyl-ethoxy)-cyclohexanecarboxylic acid ethyl ester (RS)-trans-4-(2-Acetoxy-1-methyl-ethoxy)-cyclohexanecarboxylic acid ethyl ester and (RS)-cis-4-(2-acetoxy-1-methyl-ethoxy)-cyclohexanecarboxylic acid ethyl ester were obtained from acetoxyacetone according to general procedure I after separation by flash-column chromatography.

(RS)-trans-4-(2-Acetoxy-1-methyl-ethoxy)-cyclohexanecarboxylic acid ethyl ester was obtained as light yellow oil in 13% yield. MS m/e: 273 (M+H⁺)

(RS)-cis-4-(2-Acetoxy-1-methyl-ethoxy)-cyclohexanecarboxylic acid ethyl ester was obtained as light yellow oil in 41% yield. MS m/e: 273 (M+H⁺)

4-Alkoxy-cyclohexanecarboxylic acid ester 17

(RS)-trans-4-(3,3,3-Trifluoro-1-methyl-propoxy)-cyclohexanecarboxylic acid ethyl ester and 4-Alkoxy-cyclohexanecarboxylic acid ester 18

(RS)-cis-4-(3,3,3-Trifluoro-1-methyl-propoxy)-cyclohexanecarboxylic acid ethyl ester (RS)-trans-4-(3,3,3-Trifluoro-1-methyl-propoxy)-cyclohexanecarboxylic acid ethyl ester and (RS)-cis-4-(3,3,3-trifluoro-1-methyl-propoxy)-cyclohexanecarboxylic acid ethyl ester were obtained from acetoxyacetone according to general procedure I after separation by flash-column chromatography.

(RS)-trans-4-(3,3,3-Trifluoro-1-methyl-propoxy)-cyclohexanecarboxylic acid ethyl ester was obtained as colorless oil in 9% yield. MS (EI) m/e: 282 (M⁺)

(RS)-cis-4-(3,3,3-Trifluoro-1-methyl-propoxy)-cyclohexanecarboxylic acid ethyl ester was obtained as colorless oil in 4% yield. MS m/e: 283 (M+H⁺)

4-Alkoxy-cyclohexanecarboxylic acid ester 19 cis/trans-4-(2-Benzyloxy-1-benzyloxymethyl-ethoxy)-cyclohexanecarboxylic acid ethyl ester The title compound was obtained as colorless oil in 49% yield from 1,3-dibenzyloxy-2-propanol according to general procedure IIA. MS m/e: 427 (M+H⁺)

4-Alkoxy-cyclohexanecarboxylic acid ester 20 cis/trans-4-(2-Hydroxy-1-hydroxymethyl-ethoxy)-cyclohexanecarboxylic acid ethyl ester (3:7)

To an argon purged solution of cis/trans-4-(2-benzyloxy-1-benzyloxymethyl-ethoxy)-cyclohexanecarboxylic acid ethyl ester (2.30 g, 5.39 mmol) in acetic acid (54 ml) was added palladium on charcoal 10% (0.57 g). The reaction mixture was purged with hydrogen gas and stirred at room temperature for 3 h under an atmosphere of hydrogen gas. The catalyst was removed by filtration over Decalite. The filtrate was concentrated in vacuo. Flash-chromatography with n-heptane/ethyl acetate as eluent gave the title compound (0.74 g, 56%) as colorless oil. MS m/e: 247 (M+H⁺)

4-Alkoxy-cyclohexanecarboxylic acid ester 21

(RS)-cis/trans-4-[1-Hydroxymethyl-2-(toluene-4-sulfonyloxy)-ethoxy]-cyclohexanecarboxylic acid ethyl ester (3:7)

To a solution of cis/trans-4-(2-hydroxy-1-hydroxymethyl-ethoxy)-cyclohexanecarboxylic acid ethyl ester (3:7) (0.74 g, 3.0 mmol) and triethylamine (0.42 ml, 3.0 mmol) in dichloromethane (30 ml) a catalytic amount of 4-N,N-dimethylaminopyridine was added. A solution of p-toluenesulfonyl chloride (0.57 g, 3.0 mmol) in dichloromethane (10 ml) was added dropwise at room temperature. Stirring for 16 h was followed by partitioning between ethyl acetate (100 ml) and 0.5 M aqueous hydrogen chloride solution (50 ml). The layers were separated. The aqueous layer was extracted with two portions of ethyl acetate. The combined organic layers were washed with one portion of brine, dried over anhydrous sodium sulfate and concentrated in vacuo. Flash-chromatography with n-heptane/ethyl acetate as eluent gave the title compound (0.46 g, 38%) as colorless oil. MS m/e: 401 (M+H⁺)

4-Alkoxy-cyclohexanecarboxylic acid ester 22 cis/trans-4-(Tetrahydro-pyran-4-yloxy)-cyclohexanecarboxylic acid ethyl ester (7:1)

The title compound was obtained as colorless oil in 49% yield from tetrahydro-pyran-4-one according to general procedure I. MS m/e: 257 (M+H⁺)

4-Alkoxy-cyclohexanecarboxylic acid ester 23 cis/trans-4-Methylsulfanylthiocarboxyoxy-cyclohexanecarboxylic acid ethyl ester

To a solution of ethyl 4-hydroxycyclohexane carboxylate (2:1) (3.0 g, 17 mmol) in N,N-dimethylformamide (35 ml) was added sodium hydride (1.0 g, 21 mmol, 50% in mineral oil) at 0-5° C. The reaction mixture was stirred for 10 minutes at 0° C. and for 45 minutes at room temperature. Carbon disulfide (2.1 ml, 35 mmol) was added dropwise at 0-5° C. over a period of 10 minutes. The reaction mixture was stirred for 7 h at room temperature. Iodomethane (1.3 ml, 21 mmol) was added dropwise at 0-5° C. Stirring for 16 h at room temperature was followed by quenching with saturated aqueous ammonium chloride solution (6 ml). The reaction mixture was partitioned between saturated aqueous ammonium chloride solution (150 ml) and tert-butyl methyl ether (150 ml). The layers were separated. The aqueous layer was extracted with two 150-ml portions of tert-butyl methyl ether. The combined organic layers were washed with two 50-ml portions of water and one 50-ml portion of brine, dried over anhydrous sodium sulfate and concentrated in vacuo. Flash-chromatography with n-heptane/ethyl acetate as eluent gave the title compound (0.46 g, 38%) as colorless oil. MS m/e: 263 (M+H⁺)

4-Alkoxy-cyclohexanecarboxylic acid ester 24 trans-4-tert-Butoxy-cyclohexanecarboxylic acid ethyl ester and

4-Alkoxy-cyclohexanecarboxylic acid ester 25 cis-4-tert-Butoxy-cyclohexanecarboxylic acid ethyl ester

To a solution of cis/trans-4-hydroxycyclohexane carboxylic acid ethyl ester (2:1) (1.0 g, 5.8 mmol) and di-tort-butyl dicarbonate (2.9 g, 13.4 mmol) in dichloromethane (6 ml) was added anhydrous magnesium perchlorate (0.13 g, 0.58 mmol) which was previously activated in high vacuo (ca. 1 mbar) at 150° C. for 1 h. Stirring for 16 h at 40° C. was followed by partitioning between dichloromethane (50 ml) and water (30 ml). The layers were separated. The aqueous layer was extracted with one 50-ml portion of dichloromethane. The combined organic layers were dried over anhydrous sodium sulfate and concentrated in vacuo. Purification by flash-chromatography with n-heptane/tert-butyl methyl ether as eluent gave pure trans-4-tert-butoxy-cyclohexanecarboxylic acid ethyl ester and cis-4-tert-butoxy-cyclohexanecarboxylic acid ethyl ester.

trans-4-tert-Butoxy-cyclohexanecarboxylic acid ethyl ester was obtained as colorless oil in 8% yield. MS (EI) m/e: 228 ($M^{+\cdot}$ 1%), 155 $[M-C_4H_9O]^+$, 61%)

cis-4-tert-Butoxy-cyclohexanecarboxylic acid ethyl ester was obtained as colorless oil in 8% yield. MS m/e: 229 $(M+H^+)$

4-Alkoxy-cyclohexanecarboxylic acid intermediates of formula (XII)

4-Alkoxy-cyclohexanecarboxylic acid 1 cis/trans-4-(Oxetan-3-yloxy)-cyclohexanecarboxylic acid (1:3)

To a solution of cis/trans-4-[1-hydroxymethyl-2-(toluene-4-sulfonyloxy)-ethoxy]-cyclohexanecarboxylic acid ethyl ester (3:7) (0.46 g, 1.2 mmol) in toluene (11.5 ml) was added potassium tert-butoxide (0.14 g, 1.3 mmol). The reaction mixture was heated at reflux for 20 h. After cooling to room temperature the mixture was partitioned between ethyl acetate (50 ml) and 1 M aqueous hydrogen chloride solution (30 ml). The layers were separated. The aqueous layer was extracted with two 50-ml portions of ethyl acetate. The combined organic layers were dried over anhydrous sodium sulfate and concentrated in vacuo. The residue was dissolved in 1,4-dioxane (12 ml) and 2 M aqueous sodium hydroxide solution (5.7 ml, 12 mmol). After stirring at room temperature for 16 h the mixture was partitioned between tert-butyl methyl ether (30 ml) and 1 M aqueous sodium hydroxide solution (50 ml). The layers were separated. The organic layer was extracted with one 50-ml portion of 1 M aqueous sodium hydroxide solution. The combined aqueous layers were acidified by addition of concentrated hydrochloric acid solution and crushed ice (50 g) and extracted with three 50-ml portions of ethyl acetate. The combined organic layers were dried over anhydrous sodium sulfate and concentrated in vacuo. Flash-chromatography with n-heptane/ethyl acetate as eluent gave the title compound (0.12 g, 50%) as off-white solid. MS m/e: 199 $(M+H^+)$

4-Alkoxy-cyclohexanecarboxylic acid 2 cis/trans-4-(Tetrahydro-pyran-4-yloxy)-cyclohexanecarboxylic acid (1:2)

A mixture of cis/trans-4-(tetrahydro-pyran-4-yloxy)-cyclohexanecarboxylic acid ethyl ester (7:1) (0.385 g, 1.50 mmol) and sodium ethoxide (0.204 g, 3.00 mmol) in dry toluene (1.5 ml) was heated at reflux for 20 h. The reaction mixture was cooled to room temperature, diluted with 1,4-dioxane (7.5 ml) and 2 M aqueous sodium hydroxide solution (7.5 ml). Stirring for 16 h was followed by partitioning between 2 M aqueous sodium hydroxide solution (50 ml) and dichloromethane. The layers were separated. The aqueous layer was extracted with one portion of dichloromethane. The combined organic layers were washed with two 50 ml portions of 2 M aqueous sodium hydroxide solution. The combined aqueous layers were acidified to pH 1 by addition of concentrated hydrochloric acid solution (100 ml). The aqueous layer was extracted with two 150-ml portions of dichloromethane. The combined organic layers from the acidic extraction were dried over anhydrous sodium sulfate and dried in vacuo to give the title compound (0.358 g, 93%) as yellow solid. MS m/e: 229 $(M+H^+)$

4-Alkoxy-cyclohexanecarboxylic acid 3 cis/trans-4-Trifluoromethoxy-cyclohexanecarboxylic acid

To a suspension of N-bromosuccinimid (4.95 g, 27.8 mmol) in dichloromethane (13 ml) were consecutively added dry pyridine (2.5 ml) and hydrogen fluoride pyridine complex 70% (5.80 ml, 223 mmol) at −45° C. The mixture was allowed to warm to 0° C. and stirred for 10 minutes. A solution of cis/trans-4-methylsulfanylthiocarboxyoxy-cyclohexanecarboxylic acid ethyl ester (1.46 g, 5.6 mmol) in dichloromethane (10 ml) was added dropwise. Stirring for 1 h at 0° C. was followed by partitioning between tert-butyl methyl ether (150 m) and a mixture of saturated aqueous sodium bicarbonate solution (20 ml), 40% aqueous sodium hydrogen sulfite solution (20 ml) and 1 M aqueous sodium hydroxide solution (20 ml). The pH was adjusted to 9-10 by addition of further 1 M aqueous sodium hydroxide solution (210 ml). The layers were separated. The aqueous layer was extracted with two 100-ml portions of tert-butyl methyl ether. The combined organic layers were washed with two 50-ml portions of 1 M aqueous hydrogen chloride solution and one 50-ml portion of brine, dried over anhydrous sodium sulfate and concentrated in vacuo. The crude cis/trans-4-trifluoromethoxy-cyclohexanecarboxylic acid ethyl ester (0.57 g) was dissolved in 1,4-dioxane (18 ml) and 2 M aqueous sodium hydroxide solution (11.8 ml, 23.7 mmol). Stirring at room temperature for 18 h was followed by addition of 1 M aqueous hydrogen chloride solution (20 ml). The reaction mixture was extracted with three 100-ml portions of ethyl acetate. The combined organic layers were dried over anhydrous sodium sulfate and concentrated in vacuo to give the title compound (0.37 g, 73%) as amorphous light brown solid, which was used in the next step without further purification. MS m/e: 211 $(M-H^+)$

Hydrazide Intermediates of Formula (II)

General Procedure IIIA: Hydrazide Formation from 4-Alkoxy-Cyclohexanecarboxylic Acid Ester A mixture of a 4-alkoxy-cyclohexanecarboxylic acid ester (1 eq) and hydrazine hydrate (2-6 eq) in n-butanol (0.2-1 M)

is heated at reflux for 16-72 h. After cooling to room temperature the reaction mixture is partitioned between an organic solvent such as ethyl acetate or dichloromethane and water. The layers are separated and the aqueous layer is extracted with two portions of organic solvent. The combined organic layers are dried over anhydrous sodium sulfate and concentrated in vacuo to give the crude title compound, which is used in the next step without further purification.

General Procedure IIIB: Hydrazide Formation from 4-Alkoxy-Cyclohexanecarboxylic Acid To a solution of a 4-alkoxy-cyclohexanecarboxylic acid (1 eq) and triethylamine (1 eq) in tetrahydrofuran (0.2 M) is added ethyl chloroformate at 0° C. The reaction mixture is stirred for 1 h. The ammonium salts are removed by filtration. The filtrate is added to a cold solution of hydrazine hydrate (2 eq) in methanol (0.2 M). The reaction mixture is stirred at room temperature for 2-16 h. The solvent is evaporated under reduced pressure and the residue is partitioned between an organic solvent such as ethyl acetate or dichloromethane and water. The organic layer is separated. The aqueous layer is extracted with two or three portions of organic solvent. The combined organic layers are dried over anhydrous sodium sulfate and concentrated in vacuo to give the crude title compound which is used in the next step without further purification.

Hydrazide 1 cis/trans-4-Methoxy-cyclohexanecarboxylic acid hydrazide (1:1)

The title compound was obtained as colorless amorphous solid in 55% yield from cis/trans-4-methoxy-cyclohexanecarboxylic acid according to general procedure IIIB. MS m/e: 173 (M+H$^+$)

Hydrazide 2 trans-4-Ethoxy-cyclohexanecarboxylic acid hydrazide

The title compound was obtained as white solid in 70% yield from trans-4-ethoxy-cyclohexane-carboxylic acid ethyl ester according to general procedure IIIA. MS m/e: 187 (M+H$^+$)

Hydrazide 3 cis-4-Ethoxy-cyclohexanecarboxylic acid hydrazide

The title compound was obtained as white solid in 76% yield from cis-4-ethoxy-cyclo hexanecarboxylic acid ethyl ester according to general procedure IIIA. MS m/e: 187 (M+H$^+$)

Hydrazide 4 trans-4-Isopropoxy-cyclohexanecarboxylic acid hydrazide

The title compound was obtained as off-white solid in 70% yield from trans-4-isoproxy-cyclohexanecarboxylic acid ethyl ester according to general procedure IIIA. MS m/e: 201 (M+H$^+$)

Hydrazide 5 cis-4-Isopropoxy-cyclohexanecarboxylic acid hydrazide

The title compound was obtained as white solid in 86% yield from cis-4-isoproxy-cyclo hexanecarboxylic acid ethyl ester according to general procedure IIIA. MS m/e: 201 (M+H$^+$)

Hydrazide 6

(RS)-trans-4-sec-Butoxy-cyclohexanecarboxylic acid hydrazide

The title compound was obtained as white solid in 93% yield from (RS)-trans-4-sec-butoxy-cyclohexanecarboxylic acid ethyl ester according to general procedure IIIA. MS (EI) m/e: 214 (M$^+$)

Hydrazide 7 trans-4-Cyclobutoxy-cyclohexanecarboxylic acid hydrazide

The title compound was obtained as white solid in 93% yield from trans-4-cyclobutoxy-cyclohexanecarboxylic acid ethyl ester according to general procedure IIIA. MS m/e: 213 (M+H$^+$)

Hydrazide 8 cis-4-Cyclobutoxy-cyclohexanecarboxylic acid hydrazide

The title compound was obtained as white solid in 91% yield from cis-4-cyclobutoxy-cyclohexanecarboxylic acid ethyl ester according to general procedure IIIA. MS m/e: 213 (M+H$^+$)

Hydrazide 9 trans-4-Cyclopentyloxy-cyclohexanecarboxylic acid hydrazide

The title compound was obtained as white solid in 80% yield from trans-4-cyclopentyloxy-cyclohexanecarboxylic acid ethyl ester according to general procedure IIIA. MS (EI) m/e: 226 (M$^+$)

Hydrazide 10 trans-4-Cyclohexyloxy-cyclohexanecarboxylic acid hydrazide

The title compound was obtained as white solid in 88% yield from trans-4-cyclohexyloxy-cyclohexanecarboxylic acid ethyl ester according to general procedure IIIA. MS m/e: 241 (M+H$^+$)

Hydrazide 11 cis-4-Cyclohexyloxy-cyclohexanecarboxylic acid hydrazide

The title compound was obtained as white solid in 88% yield from cis-4-cyclohexyloxy-cyclohexanecarboxylic acid ethyl ester according to general procedure IIIA. MS m/e: 241 (M+H$^+$)

Hydrazide 12

(RS)-trans-4-(2-Methoxy-1-methyl-ethoxy)-cyclohexanecarboxylic acid hydrazide

The title compound was obtained as white solid in 75% yield from (RS)-trans-4-(2-methoxy-1-methyl-ethoxy)-cyclohexanecarboxylic acid ethyl ester according to general procedure IIIA. MS m/e: 231 (M+H$^+$)

Hydrazide 13

(RS)-trans-4-(2-Hydroxy-1-methyl-ethoxy)-cyclohexanecarboxylic acid hydrazide

The title compound was obtained as colorless amorphous solid in 97% yield from (RS)-4-(2-acetoxy-1-methylethoxy)-cyclohexanecarboxylic acid ethyl ester according to general procedure IIIA. MS m/e: 217 (M+H$^+$)

Hydrazide 14

(RS)-trans-4-(3,3,3-Trifluoro-1-methyl-propoxy)-cyclohexanecarboxylic acid hydrazide The title compound was obtained as white solid in 84% yield from (RS)-trans-4-(3,3,3-trifluoro-1-methyl-propoxy)-cyclohexanecarboxylic acid ethyl ester according to general procedure IIIA. MS m/e: 269 (M+H$^+$)

Hydrazide 15 cis/trans-4-(Oxetan-3-yloxy)-cyclohexanecarboxylic acid hydrazide (1:3)

The title compound was obtained as white solid in 53% yield from cis/trans 4-(oxetan-3-yloxy)-cyclohexanecarboxylic acid (1:3) according to general procedure IIIB. MS m/e: 215 (M+H$^+$)

Hydrazide 16 cis/trans-4-(Tetrahydro-pyran-4-yloxy)-cyclohexanecarboxylic acid hydrazide (1:2)

The title compound was obtained as yellow solid in 88% yield from cis/trans-4-(tetrahydro-pyran-4-yloxy)-cyclohexanecarboxylic acid (1:2) according to general procedure IIIB. MS m/e: 243 (M+H$^+$)

Hydrazide 17 cis/trans-4-Trifluoromethoxy-cyclohexanecarboxylic acid hydrazide

The title compound was obtained as yellow solid in 86% yield from cis/trans-4-trifluoromethoxy-cyclohexanecarboxylic acid according to general procedure IIIB. MS m/e: 227 (M+H$^+$)

Hydrazide 18 trans-4-tert-Butoxy-cyclohexanecarboxylic acid hydrazide

The title compound was obtained as white solid in 81% yield from trans-4-tert-butoxy-cyclohexanecarboxylic acid ethyl ester according to general procedure IIIA. MS m/e: 215 (M+H$^+$)

Hydrazide 19 cis-4-tert-Butoxy-cyclohexanecarboxylic acid hydrazide

The title compound was obtained as light yellow solid in quantitative yield from cis-4-tert-butoxy-cyclohexanecarboxylic acid ethyl ester according to general procedure IIIA. MS m/e: 215 (M+H$^+$)

Thiolactam Intermediates of Formula (III)

7-Chloro-2-thioxo-1,2,3,5-tetrahydro-benzo[e][1,4]diazepine-4-carboxylic acid tert-butyl ester a) 4-Chloro-2-chloromethyl-1-nitro-benzene To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 min while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M$^+$).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H$^+$).

c) [tert-Butoxycarbonyl-(5-chloro-2-nitro-benzyl)-amino]-acetic acid ethyl ester A solution of (5-chloro-2-nitro-benzylamino)-acetic acid ethyl ester (110 g, 0.403 mol), di-tert-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H$^+$).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol). The reaction mixture was purged with argon after 15 min. After addition of the palladium catalyst (10% on activated charcoal, 7.9 g, 0.0074 mol) the mixture was hydrogenated at ambient pressure during a period of ca. 48 h until ca. 13 l of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H$^+$).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]-acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 min the precipitate was collected by filtration. The layers were separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid. MS m/e: 295 (M−H$^+$).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tort-butyl methyl ether. The precipitate was removed by filtration and the filtrate was concentrated to dryness. The residue was crystallized from hot ethanol to give the title compound (37.5 g, 86.4%) as light yellow solid. MS m/e: 311 (M−H$^+$).

7-Fluoro-2-thioxo-1,2,3,5-tetrahydro-benzo[e][1,4]diazepine-4-carboxylic acid tert-butyl ester The title compound was obtained as light yellow solid in comparable yields according to the procedures described above for the synthesis of 7-chloro-2-thioxo-1,2,3,5-tetrahydro-benzo[e][1,4]diazepine-4-carboxylic acid tert-butyl ester using 5-fluoro-2-nitrobenzyl alcohol instead of 5-chloro-2-nitrobenzyl alcohol in step a). MS m/e: 297 (M−H$^+$).

General Procedure IV: Condensation of Hydrazide and Thiolactam to Triazole

A mixture of a hydrazide derivative of formula (II) (1-1.5 eq) and a thiolactam of formula (III) (1 eq) in n-butanol (0.1-0.2 M) is heated at reflux for 16-72 h. After cooling to room temperature the solvent is evaporated and the residue is purified by flash-chromatography to give a compound of formula (I). When a thiolactam of formula (III-1) (compounds of formula (III) in which R$^2$ is tert-butoxycarbonyl) is used the N-tert-butoxycarbonyl group of the resulting triazole product of formula (I-a) can be partially or completely cleaved thermally, and a secondary amine derivative of formula (I-b) is obtained in addition or as the sole product.

General Procedure V: Cleavage of N-tert-butoxycarbonyl (N—BOC) Group

A solution of an N—BOC derivative of general formula (I-a) (1 eq) in 1.25 M methanolic or 1.5 M ethanolic hydrogen chloride solution (10-20 eq HCl) is heated at 50° C. for 15-60 min. After cooling to room temperature the reaction mixture is concentrated in vacuo to give a secondary amine derivative of general formula (I-b) as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula (I-b).

General Procedure VI: Reductive N-Alkylation

A mixture of a compound of formula (I-b) as free base or as hydrochloride salt (1 eq, 0.1-0.2 M), triethylamine (1 eq when the hydrochloride salt of a compound of formula (I-b) is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl derivative of formula (I).

Example 1 cis-8-Chloro-1-(4-methoxy-cyclohexyl)-5-methyl-5,6-dihydro-4H-2,3,5,10b-tetraaza-benzo[e]azulene a) cis/trans-8-Chloro-1-(4-methoxy-cyclohexyl)-4H,6H-2,3,5,10b-tetraaza-benzo[e]azulene-5-carboxylic acid tert-butyl ester (1:1)

Hydrazide: cis/trans-4-Methoxy-cyclohexanecarboxylic acid hydrazide (1:1) Thiolactam: 7-Chloro-2-thioxo-1,2,3,5-tetrahydro-benzo[e][1,4]diazepine-4-carboxylic acid tert-butyl ester. The title compound was obtained as brown solid in 53% yield using general procedure IV. MS m/e: 433 (M+H$^+$)

b) cis/trans-8-Chloro-1-(4-methoxy-cyclohexyl)-5,6-dihydro-4H-2,3,5,10b-tetraaza-benzo[e]azulene (1:1)

The title compound was obtained as light brown solid in quantitative yield from cis/trans-8-chloro-1-(4-methoxy-cyclohexyl)-4H,6H-2,3,5,10b-tetraaza-benzo[e]azulene-5-carboxylic acid tert-butyl ester (1:1) using general procedure V. MS m/e: 333 (M+H$^+$)

c) cis-8-Chloro-1-(4-methoxy-cyclohexyl)-5-methyl-5,6-dihydro-4H-2,3,5,10b-tetraaza-benzo[e]azulene The title compound was obtained as white solid in 4% yield from cis/trans-8-chloro-1-(4-methoxy-cyclohexyl)-5,6-dihydro-4H-2,3,5,10b-tetraaza-benzo[e]azulene (1:1) and paraformaldehyde according to general procedure VI after purification by preparative HPLC on a Chiralpak AD column with n-heptane/2-propanol (7:3) as eluent. MS m/e: 347 (M+H$^+$).

Example 2 trans-8-Chloro-1-(4-ethoxy-cyclohexyl)-4H,6H-2,3,5,10b-tetraaza-benzo[e]azulene-5-carboxylic acid tert-butyl ester The title compound was obtained as white solid in 77% yield using general procedure IV.

Hydrazide: trans-4-Ethoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester MS m/e: 447 (M+H$^+$)

Example 3 trans-8-Chloro-1-(4-ethoxy-cyclohexyl)-5,6-dihydro-4H-2,3,5,10b-tetraaza-benzo[e]azulene hydrochloride The title compound was obtained as white solid in quantitative yield from trans-8-chloro-1-(4-ethoxy-cyclohexyl)-4H,6H-2,3,5,10b-tetraaza-benzo[e]azulene-5-carboxylic acid tert-butyl ester using general procedure V. MS m/e: 347 (M+H')

Example 4 trans-8-Chloro-1-(4-ethoxy-cyclohexyl)-5-methyl-5,6-dihydro-4H-2,3,5,10b-tetraaza-benzo[e]azulene The title compound was obtained as white solid in 79% yield trans-8-chloro-1-(4-ethoxy-cyclohexyl)-5,6-dihydro-4H-2,3,5,10b-tetraaza-benzo[e]azulene hydrochloride and para-formaldehyde using general procedure VI. MS m/e: 361 (M+H$^+$).

Example 5 cis-8-Chloro-1-(4-ethoxy-cyclohexyl)-4H,6H-2,3,5,10b-tetraaza-benzo[e]azulene-5-carboxylic acid tert-butyl ester The title compound was obtained as white solid in 37% yield using general procedure IV. Hydrazide: cis-4-Ethoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 447 (M+H$^+$)

Example 6 cis-8-Chloro-1-(4-ethoxy-cyclohexyl)-5,6-dihydro-4H-2,3,5,10b-tetraaza-benzo[e]azulene hydrochloride The title compound was obtained as white solid in 91% yield from cis-8-chloro-1-(4-ethoxy-cyclohexyl)-4H,6H-2,3,5,10b-tetraaza-benzo[e]azulene-5-carboxylic acid tert-butyl ester using general procedure V. MS m/e: 347 (M+H$^+$)

Example 7 cis-8-Chloro-1-(4-ethoxy-cyclohexyl)-5-methyl-5,6-dihydro-4H-2,3,5,10b-tetraaza-benzo[e]azulene The title compound was obtained as white solid in 50% yield from trans-8-chloro-1-(4-ethoxy-cyclohexyl)-5,6-dihydro-4H-2,3,5,10b-tetraaza-benzo[e]azulene hydrochloride and paraformaldehyde using general procedure VI. MS m/e: 361 (M+H').

Example 8 trans-8-Chloro-1-(4-isopropoxy-cyclohexyl)-4H,6H-2,3,5,10b-tetraaza-benzo[e]azulene-5-carboxylic acid tert-butyl ester The title compound was obtained as white solid in 38% yield using general procedure IV.
Hydrazide: trans-4-Isopropoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester MS m/e: 461 (M+H$^+$)

Example 9 trans-8-Chloro-1-(4-isopropoxy-cyclohexyl)-5,6-dihydro-4H-2,3,5,10b-tetraaza-benzo[e]azulene hydrochloride The title compound was obtained as white solid in quantitative yield from trans-8-chloro-1-(4-isopropoxy-cyclohexyl)-4H,6H-2,3,5,10b-tetraaza-benzo[e]azulene-5-carboxylic acid tert-butyl ester using general procedure V. MS m/e: 361 (M+H$^+$)

Example 10 trans-8-Chloro-1-(4-isopropoxy-cyclohexyl)-5-methyl-5,6-dihydro-4H-2,3,5,10b-tetraaza-benzo[e]azulene The title compound was obtained as white solid in 78% yield from trans-8-chloro-1-(4-isopropoxy-cyclohexyl)-5,6-dihydro-4H-2,3,5,10b-tetraaza-benzo[e]azulene hydrochloride and paraformaldehyde using general procedure VI. MS m/e: 375 (M+H$^+$).

Example 11 trans-8-Chloro-1-(4-isopropoxy-cyclohexyl)-5-methanesulfonyl-5,6-dihydro-4H-2,3,5,10b-tetraaza-benzoazulene To a solution of trans-8-chloro-1-(4-isopropoxy-cyclohexyl)-5,6-dihydro-4H-2,3,5,10b-tetraaza-benzo[e]azulene hydrochloride (0.070 g, 0.18 mmol) and triethylamine (0.052 ml, 0.37 mmol) in dichloromethane (5 ml) was added methanesulfonyl chloride (0.015 ml, 0.19 mmol) at room temperature. After stirring for 19 h the reaction mixture was concentrated in vacuo. Flash-chromatography with n-heptane/2-propanol as eluent gave the title compound (0.004 g, 5%) as yellow solid. MS m/e: 439 (M+H$^+$).

Example 12 trans-2-[8-Chloro-1-(4-isopropoxy-cyclohexyl)-4H,6H-2,3,5,10b-tetraaza-benzoazulen-5-yl]-ethanol The title compound was obtained as white solid in 50% yield from trans-8-chloro-1-(4-isopropoxy-cyclohexyl)-5,6- dihydro-4H-2,3,5,10b-tetraaza-benzo[e]azulene hydrochloride and glycolaldehyde using general procedure VI. MS m/e: 405 (M+H$^+$)

Example 13 trans-8-Chloro-1-(4-isopropoxy-cyclohexyl)-5-isopropyl-5,6-dihydro-4H-2,3,5,10b-tetraaza-benzoazulene The title compound was obtained as white solid in 25% yield from trans-8-chloro-1-(4-isopropoxy-cyclohexyl)-5,6-dihydro-4H-2,3,5,10b-tetraaza-benzo[e]azulene hydrochloride and acetone using general procedure VI. MS m/e: 403 (M+H$^+$)

Example 14 trans-8-Chloro-1-(4-isopropoxy-cyclohexyl)-4H,6H-2,3,5,10b-tetraaza-benzoazulene-5-sulfonic acid dimethylamide To a solution of trans-8-chloro-1-(4-isopropoxy-cyclohexyl)-5,6-dihydro-4H-2,3,5,10b-tetraaza-benzo[e]azulene hydrochloride (0.070 g, 0.18 mmol) and triethylamine (0.037 ml, 0.26 mmol) in dichloromethane (3 ml) was added N,N-dimethylsulfamoyl chloride (0.028 ml, 0.26 mmol) at room temperature. After stirring for 65 h the reaction mixture was concentrated in vacuo. Flash-chromatography with n-heptane/2-propanol as eluent gave the title compound (0.063 g, 77%) as white solid. MS m/e: 468 (M+H$^+$).

Example 15 trans-8-Chloro-1-(4-isopropoxy-cyclohexyl)-5-pyridin-2-ylmethyl-5,6-dihydro-4H-2,3,5,10b-tetraaza-benzoazulene To a mixture of trans-8-chloro-1-(4-isopropoxy-cyclohexyl)-5,6-dihydro-4H-2,3,5,10b-tetraaza-benzo[e]azulene hydrochloride (0.070 g, 0.18 mmol) and potassium carbonate (0.073 ml, 0.53 mmol) in acetonitrile (1 ml) was added 2-(bromomethyl)pyridine hydrobromide (0.048 g, 0.18 mmol) at room temperature. Stirring for 20 h at 50° C. was followed by partitioning between 1 M aqueous sodium hydroxide solution (30 ml) and dichloromethane (30 ml). The layers were separated. The aqueous layer was extracted with two 30-ml portions of dichloromethane. The combined organic layers were dried over anhydrous sodium sulfate and concentrated in vacuo. Purification by flash-chromatography with n-heptane/2-propanol as eluent gave the title compound (0.046 g, 58%) as yellow oil. MS m/e: 452 (M+H$^+$).

Example 16 trans-Acetic acid 2-[8-chloro-1-(4-isopropoxy-cyclohexyl)-4H,6H-2,3,5,10b-tetraaza-benzoazulen-5-yl]-2-oxo-ethyl ester To a solution of trans-8-chloro-1-(4-isopropoxy-cyclohexyl)-5,6-dihydro-4H-2,3,5,10b-tetraaza-benzo[e]azulene hydrochloride (0.090 g, 0.23 mmol) and triethylamine (0.066 ml, 0.48 mmol) in dichloromethane (5 ml) was added acetoxyacetyl chloride (0.031 g, 0.25 mmol) at room temperature. After stirring for 19 h the reaction mixture was concentrated in vacuo. Flash-chromatography with n-heptane/2-propanol as eluent gave the title compound (0.073 g, 70%) as white solid. MS m/e: 461 (M+H$^+$).

Example 17 trans-1-[8-Chloro-1-(4-isopropoxy-cyclohexyl)-4H,6H-2,3,5,10b-tetraaza-benzoazulen-5-yl]-2-hydroxy-ethanone To a solution of trans-acetic acid 2-[8-chloro-1-(4-isopropoxy-cyclohexyl)-4H,6H-2,3,5,10b-tetraaza-benzoazulen-5-yl]-2-oxo-ethyl ester in methanol (5 ml) was added one drop of a 30% methanolic sodium methoxide solution at room temperature. Stirring for 40 minutes was followed by quenching with water. The mixture was extracted with three portions of tert-butyl methyl ether. The combined org layers were dried over anhydrous sodium sulfate and concentrated in vacuo. Flash-chromatography with n-heptane/2-propanol as eluent gave the title compound (0.033 g, 49%) as white solid. MS m/e: 419 (M+H$^+$).

Example 18 trans-1-[8-Chloro-1-(4-isopropoxy-cyclohexyl)-4H,6H-2,3,5,10b-tetraaza-benzoazulen-5-yl]-ethanone To a solution of trans-8-chloro-1-(4-isopropoxy-cyclohexyl)-5,6-dihydro-4H-2,3,5,10b-tetraaza-benzo[e]azulene hydrochloride (0.080 g, 0.20 mmol) and triethylamine (0.059 ml, 0.42 mmol) in dichloromethane (5 ml) was added acetyl chloride (0.016 ml, 0.22 mmol) at room temperature. After stirring for 19 h the reaction mixture was concentrated in vacuo. Flash-chromatography with n-heptane/2-propanol as eluent gave the title compound (0.062 g, 77%) as white solid. MS m/e: 403 (M+H$^+$).

Example 19 trans-8-Fluoro-1-(4-isopropoxy-cyclohexyl)-4H,6H-2,3,5,10b-tetraaza-benzo[e]azulene-5-carboxylic acid tert-butyl ester The title compound was obtained as white solid in 60% yield using general procedure IV.

Hydrazide: trans-4-Isopropoxy-cyclohexanecarboxylic acid hydrazide.

Thiolactam: 7-Fluoro-2-thioxo-1,2,3,5-tetrahydro-benzo[e][1,4]diazepine-4-carboxylic acid tert-butyl ester. MS m/e: 445 (M+H$^+$)

Example 20 trans-8-Fluoro-1-(4-isopropoxy-cyclohexyl)-5,6-dihydro-4H-2,3,5,10b-tetraaza-benzo[e]azulene hydrochloride The title compound was obtained as white solid in quantitative yield from trans-8-fluoro-1-(4-isopropoxy-cyclohexyl)-4H,6H-2,3,5,10b-tetraaza-benzo[e]azulene-5-carboxylic acid tert-butyl ester using general procedure V. MS m/e: 345 (M+H$^+$)

Example 21 trans-8-Fluoro-1-(4-isopropoxy-cyclohexyl)-5-methyl-5,6-dihydro-4H-2,3,5,10b-tetraaza-benzo[e]azulene The title compound was obtained as white solid in 77% yield from trans-8-fluoro-1-(4-isopropoxy-cyclohexyl)-5,6-dihydro-4H-2,3,5,10b-tetraaza-benzo[e]azulene hydrochloride and paraformaldehyde using general procedure VI. MS m/e: 359 (M+H$^+$).

Example 22 cis-8-Chloro-1-(4-isopropoxy-cyclohexyl)-4H,6H-2,3,5,10b-tetraaza-benzo[e]azulene-5-carboxylic acid tert-butyl ester The title compound was obtained as white solid in 64% yield using general procedure IV.
Hydrazide: cis-4-Isopropoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 461 (M+H$^+$)

Example 23 cis-8-Chloro-1-(4-isopropoxy-cyclohexyl)-5,6-dihydro-4H-2,3,5,10b-tetraaza-benzo[e]azulene hydrochloride The title compound was obtained as white solid in quantitative yield from cis-8-chloro-1-(4-isopropoxy-cyclohexyl)-4H,6H-2,3,5,10b-tetraaza-benzo[e]azulene-5-carboxylic acid tert-butyl ester using general procedure V. MS m/e: 361 (M+H$^+$)

Example 24 cis-8-Chloro-1-(4-isopropoxy-cyclohexyl)-5-methyl-5,6-dihydro-4H-2,3,5,10b-tetraaza-benzo[e]azulene The title compound was obtained as white solid in 90% yield from cis-8-chloro-1-(4-isopropoxy-cyclohexyl)-5,6-dihydro-4H-2,3,5,10b-tetraaza-benzo[e]azulene hydrochloride and paraformaldehyde using general procedure VI. MS m/e: 359 (M+H$^+$).

Example 25

(RS)-trans-1-(4-sec-Butoxy-cyclohexyl)-8-chloro-4H,6H-2,3,5,10b-tetraaza-benzo[e]azulene-5-carboxylic acid tert-butyl ester The title compound was obtained as white solid in 71% yield using general procedure IV.
Hydrazide: (RS)-trans-4-sec-Butoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 475 (M+H$^+$)

Example 26

(RS)-trans-1-(4-sec-Butoxy-cyclohexyl)-8-chloro-5,6-dihydro-4H-2,3,5,10b-tetraaza-benzo[e]azulene hydrochloride The title compound was obtained as off-white solid in quantitative yield from (RS)-trans-1-(4-sec-butoxy-cyclohexyl)-8-chloro-4H,6H-2,3,5,10b-tetraaza-benzo[e]azulene-5-carboxylic acid tert-butyl ester using general procedure V. MS m/e: 375 (M+H$^+$)

Example 27

(RS)-trans-1-(4-sec-Butoxy-cyclohexyl)-8-chloro-5-methyl-5,6-dihydro-4H-2,3,5,10b-tetraaza-benzo[e]azulene The title compound was obtained as white solid in 66% yield from (RS)-trans-8-chloro-1-(4-isopropoxy-cyclohexyl)-5,6-dihydro-4H-2,3,5,10b-tetraaza-benzo[e]azulene hydrochloride and paraformaldehyde using general procedure VI. MS m/e: 389 (M+H$^+$).

Example 28

(+)-trans-1-(4-sec-Butoxy-cyclohexyl)-8-chloro-5-methyl-5,6-dihydro-4H-2,3,5,10b-tetraaza-benzo[e]azulene and

Example 29

(−)-trans-1-(4-sec-Butoxy-cyclohexyl)-8-chloro-5-methyl-5,6-dihydro-4H-2,3,5,10b-tetraaza-benzo[e]azulene (+)-trans-1-(4-sec-Butoxy-cyclohexyl)-8-chloro-5-methyl-5,6-dihydro-4H-2,3,5,10b-tetraaza-benzo[e]azulene and (−)-trans-1-(4-sec-butoxy-cyclohexyl)-8-chloro-5-methyl-5,6-dihydro-4H-2,3,5,10b-tetraaza-benzo[e]azulene were obtained from (RS)-trans-1-(4-sec-butoxy-cyclohexyl)-8-chloro-5-methyl-5,6-dihydro-4H-2,3,5,10b-tetraaza-benzo[e]azulene by chiral HPLC separation on a Chiralpak AD column with n-heptane/ethanol (4:1) as eluent.
(+)-trans-1-(4-sec-Butoxy-cyclohexyl)-8-chloro-5-methyl-5,6-dihydro-4H-2,3,5,10b-tetraaza-benzo[e]azulene (0.068 g, 36%) was obtained as white solid.
(MS m/e: 389 (M+H$^+$), $[\alpha]_D$=+17.2 (c=0.414, CHCl$_3$, 20° C.)
(−)-trans-1-(4-sec-Butoxy-cyclohexyl)-8-chloro-5-methyl-5,6-dihydro-4H-2,3,5,10b-tetraaza-benzo[e]azulene (0.035 g, 18%) was obtained as white solid.
(MS m/e: 389 (M+H$^+$), $[\alpha]_D$=−15.5 (c=0.414, CHCl$_3$, 20° C.).

Example 30 trans-8-Chloro-1-(4-cyclobutoxy-cyclohexyl)-4H,6H-2,3,5,10b-tetraaza-benzo[e]azulene-5-carboxylic acid tert-butyl ester The title compound was obtained as white solid in 86% yield using general procedure IV.
Hydrazide: trans-4-Cyclobutoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 473 (M+H$^+$)

Example 31 trans-8-Chloro-1-(4-cyclobutoxy-cyclohexyl)-5,6-dihydro-4H-2,3,5,10b-tetraaza-benzo[e]azulene hydrochloride The title compound was obtained as off-white solid in 87% yield from trans-8-chloro-1-(4-cyclobutoxy-cyclohexyl)-4H,6H-2,3,5,10b-tetraaza-benzo[e]azulene-5-carboxylic acid tert-butyl ester using general procedure V. MS m/e: 373 (M+H$^+$)

Example 32 trans-8-Chloro-1-(4-cyclobutoxy-cyclohexyl)-5-methyl-5,6-dihydro-4H-2,3,5,10b-tetraaza-benzo[e]azulene The title compound was obtained as white solid in 51% yield from trans-8-chloro-1-(4-cyclobutoxy-cyclohexyl)-5,6-dihydro-4H-2,3,5,10b-tetraaza-benzo[e]azulene hydrochloride and paraformaldehyde using general procedure VI. MS m/e: 387 (M+H$^+$).

Example 33 cis-8-Chloro-1-(4-cyclobutoxy-cyclohexyl)-4H,6H-2,3,5,10b-tetraaza-benzo[e]azulene-5-carboxylic acid tert-butyl ester The title compound was obtained as white solid in 95% yield using general procedure IV.
Hydrazide: cis-4-Cyclobutoxy-cyclohexanecarboxylic acid hydrazide
Thiolactam: 7-Chloro-2-thioxo-1,2,3,5-tetrahydro-benzo[c][1,4]diazepine-4-carboxylic acid tert-butyl ester. MS m/e: 473 (M+H$^+$)

Example 34 cis-8-Chloro-1-(4-cyclobutoxy-cyclohexyl)-5,6-dihydro-4H-2,3,5,10b-tetraaza-benzo[e]azulene hydrochloride The title compound was obtained as off-white solid in quantitative yield from cis-8-chloro-1-(4-cyclobutoxy-cyclohexyl)-4H,6H-2,3,5,10b-tetraaza-benzo[e]azulene-5-carboxylic acid tert-butyl ester using general procedure V. MS m/e: 373 (M+H$^+$)

Example 35 cis-8-Chloro-1-(4-cyclobutoxy-cyclohexyl)-5-methyl-5,6-dihydro-4H-2,3,5,10b-tetraaza-benzo[e]azulene The title compound was obtained as white solid in quantitative yield from cis-8-chloro-1-(4-cyclobutoxy-cyclohexyl)-5,6-dihydro-4H-2,3,5,10b-tetraaza-benzo[e]azulene hydrochloride and paraformaldehyde using general procedure VI. MS m/e: 387 (M+H$^+$).

Example 36 trans-8-Chloro-1-(4-cyclopentyloxy-cyclohexyl)-4H,6H-2,3,5,10b-tetraaza-benzo[e]azulene-5-carboxylic acid tert-butyl ester The title compound was obtained as light brown solid in 65% yield using general procedure IV. Hydrazide: trans-4-Cyclopentyloxy-cyclohexanecarboxylic acid hydrazide
Thiolactam: 7-Chloro-2-thioxo-1,2,3,5-tetrahydro-benzo[c][1,4]diazepine-4-carboxylic acid tert-butyl ester. MS m/e: 487 (M+H$^+$)

Example 37 trans-8-Chloro-1-(4-cyclopentyloxy-cyclohexyl)-5,6-dihydro-4H-2,3,5,10b-tetraaza-benzo[e]azulene hydrochloride The title compound was obtained as light brown solid in 75% yield from trans-8-chloro-1-(4-cyclopentyloxy-cyclohexyl)-4H,6H-2,3,5,10b-tetraaza-benzo[e]azulene-5-carboxylic acid tert-butyl ester using general procedure V. MS m/e: 387 (M+H$^+$)

Example 38 trans-8-Chloro-1-(4-cyclopentyloxy-cyclohexyl)-5-methyl-5,6-dihydro-4H-2,3,5,10b-tetraaza-benzo[e]azulene The title compound was obtained as white solid in 56% yield from trans-8-chloro-1-(4-cyclopentyloxy-cyclohexyl)-5,6-dihydro-4H-2,3,5,10b-tetraaza-benzo[e]azulene hydrochloride and paraformaldehyde using general procedure VI. MS m/e: 401 (M+H$^+$)

Example 39 trans-8-Chloro-1-(4-cyclohexyloxy-cyclohexyl)-4H,6H-2,3,5,10b-tetraaza-benzoazulene-5-carboxylic acid tert-butyl ester The title compound was obtained as white solid in 74% yield using general procedure IV.
Hydrazide: trans-4-Cyclohexyloxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 501 (M+H$^+$)

Example 40 trans-8-Chloro-1-(4-cyclohexyloxy-cyclohexyl)-5,6-dihydro-4H-2,3,5,10b-tetraaza-benzoazulene hydrochloride The title compound was obtained as white solid in 97% yield from trans-8-chloro-1-(4-cyclohexyloxy-cyclohexyl)-4H,6H-2,3,5,10b-tetraaza-benzoazulene-5-carboxylic acid tert-butyl ester using general procedure V. MS m/e: 401 (M+H$^+$).

Example 41 trans-8-Chloro-1-(4-cyclohexyloxy-cyclohexyl)-5-methyl-5,6-dihydro-4H-2,3,5,10b-tetraaza-benzoazulene The title compound was obtained as off-white solid in 69% yield from trans-8-chloro-1-(4-cyclohexyloxy-cyclohexyl)-5,6-dihydro-4H-2,3,5,10b-tetraaza-benzoazulene hydrochloride and paraformaldehyde using general procedure VI. MS m/e: 415 (M+H$^+$).

Example 42 cis-8-Chloro-1-(4-cyclohexyloxy-cyclohexyl)-4H,6H-2,3,5,10b-tetraaza-benzoazulene-5-carboxylic acid tert-butyl ester The title compound was obtained as white solid in 74% yield using general procedure IV.
Hydrazide: cis-4-Cyclohexyloxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 501 (M+H$^+$)

Example 43 cis-8-Chloro-1-(4-cyclohexyloxy-cyclohexyl)-5,6-dihydro-4H-2,3,5,10b-tetraaza-benzoazulene hydrochloride The title compound was obtained as white solid in quantitative yield from cis-8-chloro-1-(4-cyclohexyloxy-cyclohexyl)-4H,6H-2,3,5,10b-tetraaza-benzoazulene-5-carboxylic acid tert-butyl ester using general procedure V. MS m/e: 401 (M+H$^+$).

Example 44 cis-8-Chloro-1-(4-cyclohexyloxy-cyclohexyl)-5-methyl-5,6-dihydro-4H-2,3,5,10b-tetraaza-benzoazulene The title compound was obtained as off-white solid in 75% yield from cis-8-chloro-1-(4-cyclohexyloxy-cyclohexyl)-5,6-dihydro-4H-2,3,5,10b-tetraaza-benzoazulene hydrochloride and paraformaldehyde using general procedure VI. MS m/e: 415 (M+H$^+$).

Example 45

(RS)-trans-8-Chloro-1-[4-(2-methoxy-1-methyl-ethoxy)-cyclohexyl]-4H,6H-2,3,5,10b-tetraaza-benzo[e]azulene-5-carboxylic acid tert-butyl ester The title compound was obtained as white solid in 54% yield using general procedure IV.
Hydrazide: (RS)-trans-4-(2-Methoxy-1-methyl-ethoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 491 (M+H$^+$)

Example 46

(RS)-trans-8-Chloro-1-[4-(2-methoxy-1-methyl-ethoxy)-cyclohexyl]-5,6-dihydro-4H-2,3,5,10b-tetraaza-benzo[e]azulene hydrochloride The title compound was obtained as off-white solid in quantitative yield from (RS)-trans-8-chloro-1-[4-(2-methoxy-1-methyl-ethoxy)-cyclohexyl]-4H,6H-2,3,5,10b-tetraaza-benzo[e]-azulene-5-carboxylic acid tort-butyl ester using general procedure V. MS m/e: 391 (M+H$^+$).

Example 47

(RS)-trans-8-Chloro-1-[4-(2-methoxy-1-methyl-ethoxy)-cyclohexyl]-5-methyl-5,6-dihydro-4H-2,3,5,10b-tetraaza-benzo[e]azulene The title compound was obtained as white solid in 79% yield from (RS)-trans-8-chloro-1-[4-(2-methoxy-1-methyl-ethoxy)-cyclohexyl]-5,6-dihydro-4H-2,3,5,10b-tetraaza-benzo[e]-azulene hydrochloride and paraformaldehyde using general procedure VI. MS m/e: 405 (M+H$^+$).

Example 48

(+)-trans-8-Chloro-1-[4-(2-methoxy-1-methyl-ethoxy)-cyclohexyl]-5-methyl-5,6-dihydro-4H-2,3,5,10b-tetraaza-benzo[e]azulene and

Example 49

(−)-trans-8-Chloro-1-[4-(2-methoxy-1-methyl-ethoxy)-cyclohexyl]-5-methyl-5,6-dihydro-4H-2,3,5,10b-tetraaza-benzo[e]azulene (+)-trans-8-Chloro-1-[4-(2-methoxy-1-methyl-ethoxy)-cyclohexyl]-5-methyl-5,6-dihydro-4H-2,3,5,10b-tetraaza-benzo[e]azulene and (−)-trans-8-chloro-1-[4-(2-methoxy-1-methyl-ethoxy)-cyclohexyl]-5-methyl-5,6-dihydro-4H-2,3,5,10b-tetraaza-benzo[e]azulene were obtained from (RS)-trans-8-chloro-1-[4-(2-methoxy-1-methyl-ethoxy)-cyclohexyl]-5-methyl-5,6-dihydro-4H-2,3,5,10b-tetraaza-benzo[e]azulene by chiral HPLC separation on a Chiralpak AD column with n-heptane/ethanol (3:1) as eluent.
(+)-trans-8-Chloro-1-[4-(2-methoxy-1-methyl-ethoxy)-cyclohexyl]-5-methyl-5,6-dihydro-4H-2,3,5,10b-tetraaza-benzo[e]azulene (0.081 g, 39%) was obtained as white solid.
(MS m/e: 405 (M+H$^+$), [α]$_D$=+5.75 (c=0.574, CHCl$_3$, 20° C.)
(−)-trans-8-Chloro-1-[4-(2-methoxy-1-methyl-ethoxy)-cyclohexyl]-5-methyl-5,6-dihydro-4H-2,3,5,10b-tetraaza-benzo[e]azulene (0.078 g, 37%) was obtained as white solid
(MS m/e: 405 (M+H$^+$), [α]$_D$=−5.76 (c=0.538, CHCl$_3$, 20° C.).

Example 50

(RS)-trans-8-Chloro-1-[4-(2-hydroxy-1-methyl-ethoxy)-cyclohexyl]-4H,6H-2,3,5,10b-tetraaza-benzo[e]azulene-5-carboxylic acid tert-butyl ester The title compound was obtained as light yellow solid in 39% yield using general procedure IV. Hydrazide: (RS)- trans-4-(2-Hydroxy-1-methyl-ethoxy)-cyclohexanecarboxylic acid hydrazide. Thiolactam: 7-Chloro-2-thioxo-1,2,3,5-tetrahydro-benzo[e][1,4]diazepine-4-carboxylic acid tert-butyl ester MS m/e: 477 (M+H$^+$).

Example 51

(RS)-trans-2-[4-(8-Chloro-5,6-dihydro-4H-2,3,5,10b-tetraaza-benzo[e]azulen-1-yl)-cyclohexyloxy]-propan-1-ol hydrochloride The title compound was obtained as light brown solid in quantitative yield from (RS)-trans-8-chloro-1-[4-(2-hydroxy-1-methyl-ethoxy)-cyclohexyl]-4H,6H-2,3,5,10b-tetraaza-benzo[e]azulene-5-carboxylic acid tert-butyl ester using general procedure V. MS m/e: 377 (M+H$^+$).

Example 52

(RS)-trans-2-[4-(8-Chloro-5-methyl-5,6-dihydro-4H-2,3,5,10b-tetraaza-benzo[e]azulen-1-yl)-cyclohexyloxy]-propan-1-ol The title compound was obtained as off-white solid in 59% yield from (RS)-trans-2-[4-(8-chloro-5,6-dihydro-4H-2,3,5,10b-tetraaza-benzo[e]azulen-1-yl)-cyclohexyloxy]-propan-1-ol hydrochloride and paraformaldehyde using general procedure VI. MS m/e: 391 (M+H$^+$).

Example 53

(RS)-trans-8-Chloro-1-[4-(2-fluoro-1-methyl-ethoxy)-cyclohexyl]-5-methyl-5,6-dihydro-4H-2,3,5,10b-tetraaza-benzo[e]azulene To a solution of (RS)-trans-2-[4-(8-chloro-5-methyl-5,6-dihydro-4H-2,3,5,10b-tetraaza-benzo[e]azulen-1-yl)-cyclohexyloxy]-propan-1-ol (0.055 g, 0.14 mmol) in dichloromethane (2 ml) was added [bis(2-methoxyethyl)-amino] sulfur trifluoride (0.031 ml, 0.17 mmol) at 0-5° C. Stirring at room temperature for 18 h was followed by addition of further [bis(2-methoxyethyl)-amino]sulfur trifluoride (0.016 ml, 0.08 mmol) and stirring for 4 h. The reaction mixture was partitioned between saturated aqueous sodium bicarbonate solution (30 ml) and ethyl acetate (30 ml). The layers were separated and the aqueous layer was extracted with two 30-ml portions of ethyl acetate. The combined organic layers were dried over anhydrous sodium sulfate and concentrated in vacuo. Flash-chromatography with n-heptane/2-propanol as eluent gave the title compound (0.020 g, 36%) as white solid. MS m/e: 393 (M+H$^+$).

Example 54

(RS)-trans-8-Chloro-1-[4-(3,3,3-trifluoro-1-methyl-propoxy)-cyclohexyl]-4H,6H-2,3,5,10b-tetraaza-benzo[e]azulene-5-carboxylic acid tert-butyl ester The title compound was obtained as white solid in 28% yield using general procedure IV.
Hydrazide: trans-4-(3,3,3-Trifluoro-1-methyl-propoxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 529 (M+H$^+$)

Example 55

(RS)-trans-8-Chloro-1-[4-(3,3,3-trifluoro-1-methyl-propoxy)-cyclohexyl]-5,6-dihydro-4H-2,3,5,10b-tetraaza-benzo[e]azulene hydrochloride The title compound was obtained as off-white solid in quantitative yield from (RS)-trans-8-chloro-1-[4-(3,3,3-trifluoro-1-methyl-propoxy)-cyclohexyl]-4H,6H-2,3,5,10b-tetraaza-benzo[e]-azulene-5-carboxylic acid tert-butyl ester using general procedure V. MS m/e: 429 (M+H$^+$).

Example 56

(RS)-trans-8-Chloro-5-methyl-1-[4-(3,3,3-trifluoro-1-methyl-propoxy)-cyclohexyl]-5,6-dihydro-4H-2,3,5,10b-tetraaza-benzo[e]azulene The title compound was obtained as white solid in 55% yield from (RS)-trans-8-chloro-1-[4-(3,3,3-trifluoro-1-methyl-propoxy)-cyclohexyl]-5,6-dihydro-4H-2,3,5,10b-tetraaza-benzo[e]-azulene hydrochloride and paraformaldehyde using general procedure VI. MS m/e: 443 (M+H$^+$).

Example 57 trans-8-Chloro-1-[4-(oxetan-3-yloxy)-cyclohexyl]-4H,6H-2,3,5,10b-tetraaza-benzo[e]azulene-5-carboxylic acid tert-butyl ester The title compound was obtained as white solid in 51% yield using general procedure IV.
Hydrazide: cis/trans-4-(Oxetan-3-yloxy)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 475 (M+H$^+$)

Example 58 trans-8-Chloro-5-methyl-1-[4-(oxetan-3-yloxy)-cyclohexyl]-5,6-dihydro-4H-2,3,5,10b-tetraaza-benzo[e]azulene a) (RS)-trans-3-Chloro-2-[4-(8-chloro-5,6-dihydro-4H-2,3,5,10b-tetraaza-benzo[e]azulen-1-yl)-cyclohexyloxy]-propan-1-ol hydrochloride The title compound was obtained as off-white solid in quantitative yield from trans-8-chloro-1-[4-(oxetan-3-yloxy)-cyclohexyl]-4H,6H-2,3,5,10b-tetraaza-benzo[e]azulene-5-carboxylic acid tert-butyl ester using general procedure V. MS m/e: 411 (M+H$^+$).

b) (RS)-trans-3-Chloro-2-[4-(8-chloro-5-methyl-5,6-dihydro-4H-2,3,5,10b-tetraaza-benzo[e]azulen-1-yl)-cyclohexyloxy]-propan-1-ol The title compound was obtained as off-white solid in 87% yield from (RS)-trans-3-chloro-2-[4-(8-chloro-5,6-dihydro-4H-2,3,5,10b-tetraaza-benzo[e]azulen-1-yl)-cyclohexyloxy]-propan-1-ol hydrochloride and paraformaldehyde using general procedure VI. MS m/e: 425 (M+H$^+$).

c) trans-8-Chloro-5-methyl-1-[4-(oxetan-3-yloxy)-cyclohexyl]-5,6-dihydro-4H-2,3,5,10b-tetraaza-benzo[e]azulene To a solution of (RS)-trans-3-chloro-2-[4-(8-chloro-5-methyl-5,6-dihydro-4H-2,3,5,10b-tetraaza-benzo[e]azulen-1- yl)-cyclohexyloxy]-propan-1-ol (0.045 g, 0.11 mmol) in toluene (2 ml) was added potassium tert-butoxide (0.013 g, 0.12 mmol). The reaction mixture was heated at reflux for 2 h. After cooling to room temperature the mixture was partitioned between ethyl acetate and water. The layers were separated. The aqueous layer was extracted with two portions of ethyl acetate. The combined organic layers were dried over anhydrous sodium sulfate and concentrated in vacuo. Flash-chromatography with n-heptane/2-propanol as eluent gave the title compound (0.10 g, 24%) as white solid. MS m/e: 389 (M+H$^+$).

Example 59 trans-8-Chloro-1-[4-(tetrahydro-pyran-4-yloxy)-cyclohexyl]-4H,6H-2,3,5,10b-tetraaza-benzoazulene-5-carboxylic acid tert-butyl ester and Example 60 cis-8-Chloro-1-[4-(tetrahydro-pyran-4-yloxy)-cyclohexyl]-4H,6H-2,3,5,10b-tetraaza-benzoazulene-5-carboxylic acid tert-butyl ester trans-8-Chloro-1-[4-(tetrahydro-pyran-4-yloxy)-cyclohexyl]-4H,6H-2,3,5,10b-tetraaza-benzoazulene-5-carboxylic acid tert-butyl ester and cis-8-chloro-1-[4-(tetrahydro-pyran-4-yloxy)-cyclohexyl]-4H,6H-2,3,5,10b-tetraaza-benzoazulene-5-carboxylic acid tert-butyl ester were obtained according to general procedure IV after separation by flash-column chromatography.

Hydrazide: cis/trans-4-(Tetrahydro-pyran-4-yloxy)-cyclohexanecarboxylic acid hydrazide (1:2)

Thiolactam: 7-Chloro-2-thioxo-1,2,3,5-tetrahydro-benzo[e][1,4]diazepine-4-carboxylic acid tert-butyl ester trans-8-Chloro-1-[4-(tetrahydro-pyran-4-yloxy)-cyclohexyl]-4H,6H-2,3,5,10b-tetraaza-benzoazulene-5-carboxylic acid tert-butyl ester was obtained as white foam in 26% yield. MS m/e: 503 (M+H$^+$)

cis-8-Chloro-1-[4-(tetrahydro-pyran-4-yloxy)-cyclohexyl]-4H,6H-2,3,5,10b-tetraaza-benzoazulene-5-carboxylic acid tert-butyl ester was obtained as white foam in 14% yield. MS m/e: 503 (M+H$^+$)

Example 61 trans-8-Chloro-1-[4-(tetrahydro-pyran-4-yloxy)-cyclohexyl]-5,6-dihydro-4H-2,3,5,10b-tetraaza-benzoazulene hydrochloride The title compound was obtained as white solid in quantitative yield from trans-8-chloro-1-[4-(tetrahydro-pyran-4-yloxy)-cyclohexyl]-4H,6H-2,3,5,10b-tetraaza-benzoazulene-5-carboxylic acid tert-butyl ester using general procedure V. MS m/e: 403 (M+H$^+$).

Example 62 trans-8-Chloro-5-methyl-1-[4-(tetrahydro-pyran-4-yloxy)-cyclohexyl]-5,6-dihydro-4H-2,3,5,10b-tetraaza-benzoazulene The title compound was obtained as white foam in 72% yield from trans-8-chloro-1-[4-(tetrahydro-pyran-4-yloxy)-cyclohexyl]-5,6-dihydro-4H-2,3,5,10b-tetraaza-benzoazulene hydrochloride and paraformaldehyde using general procedure VI. MS m/e: 417 (M+H$^+$).

Example 63 cis-8-Chloro-1-[4-(tetrahydro-pyran-4-yloxy)-cyclohexyl]-5,6-dihydro-4H-2,3,5,10b-tetraaza-benzoazulene hydrochloride The title compound was obtained as white solid in quantitative yield from cis-8-chloro-1-[4-(tetrahydro-pyran-4-yloxy)-cyclohexyl]-4H,6H-2,3,5,10b-tetraaza-benzoazulene-5-carboxylic acid tert-butyl ester using general procedure V. MS m/e: 403 (M+H$^+$).

Example 64 cis-8-Chloro-5-methyl-1-[4-(tetrahydro-pyran-4-yloxy)-cyclohexyl]-5,6-dihydro-4H-2,3,5,10b-tetraaza-benzoazulene The title compound was obtained as off-white solid in 72% yield from cis-8-chloro-1-[4-(tetrahydro-pyran-4-yloxy)-cyclohexyl]-5,6-dihydro-4H-2,3,5,10b-tetraaza-benzoazulene hydrochloride and paraformaldehyde using general procedure VI. MS m/e: 417 (M+H$^+$).

Example 65 trans-8-Chloro-1-(4-trifluoromethoxy-cyclohexyl)-4H,6H-2,3,5,10b-tetraaza-benzo[e]azulene-5-carboxylic acid tert-butyl ester The title compound was obtained as light yellow solid in 33% yield using general procedure IV. Hydrazide: cis/trans-4-Trifluoromethoxy-cyclohexanecarboxylic acid hydrazide Thiolactam: 7-Chloro-2-thioxo-1,2,3,5-tetrahydro-benzo[c][1,4]diazepine-4-carboxylic acid tert-butyl ester. MS m/e: 487 (M+H$^+$)

Example 66 trans-8-Chloro-1-(4-trifluoromethoxy-cyclohexyl)-5,6-dihydro-4H-2,3,5,10b-tetraaza-benzo[e]azulene hydrochloride The title compound was obtained as light yellow solid in quantitative yield from trans-8-chloro-1-(4-trifluoromethoxy-cyclohexyl)-4H,6H-2,3,5,10b-tetraaza-benzo[e]azulene-5-carboxylic acid tert-butyl ester using general procedure V. MS m/e: 387 (M+H$^+$).

Example 67 trans-8-Chloro-5-methyl-1-(4-trifluoromethoxy-cyclohexyl)-5,6-dihydro-4H-2,3,5,10b-tetraaza-benzo[e]azulene The title compound was obtained as white solid in 76% yield from trans-8-chloro-1-(4-trifluoromethoxy-cyclohexyl)-5,6-dihydro-4H-2,3,5,10b-tetraaza-benzo[e]azulene hydrochloride and paraformaldehyde using general procedure VI. MS m/e: 401 (M+H+).

Example 68 trans-1-(4-tert-Butoxy-cyclohexyl)-8-chloro-4H,6H-2,3,5,10b-tetraaza-benzo[e]azulene-5-carboxylic acid tert-butyl ester The title compound was obtained as light yellow solid in 55% yield using general procedure IV. Hydrazide: trans-4-tert-Butoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 475 (M+H+)

Example 69 cis-1-(4-tert-Butoxy-cyclohexyl)-8-chloro-4H,6H-2,3,5,10b-tetraaza-benzo[e]azulene-5-carboxylic acid tert-butyl ester The title compound was obtained as light brown solid in 63% yield using general procedure IV. Hydrazide: cis-4-tert-Butoxy-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 475 (M+H+)

The invention claimed is:
1. A compound of formula I

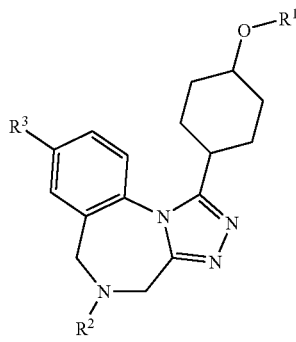

I wherein
  $R^1$ is $C_{1-12}$-alkyl, unsubstituted or substituted with one or more halo, hydroxy, cyano or $C_{1-12}$-alkoxy,
    $C_{3-7}$-cycloalkyl, unsubstituted or substituted by one or more substituents independently selected from B,
    4-7 membered heterocycloalkyl containing one or two heteroatoms selected from O, N and S, which heterocycloalkyl is unsubstituted or substituted by one or more substituents independently selected from B,
  $R^2$ is H,
    $C_{1-12}$-alkyl, unsubstituted or substituted with one or more OH, halo, cyano or $C_{1-12}$-alkoxy,
    —(CH$_2$)$_q$—R$^a$, wherein R$^a$ is phenyl or 5- or 6-membered heteroaryl, each of which is unsubstituted or substituted with one or more substituents independently selected from A,
    —(CH$_2$)$_r$NR$^i$R$^{ii}$,
    —C(O)—C$_{1-12}$-alkyl, wherein alkyl is unsubstituted or substituted with one or more OH, halo, cyano or $C_{1-12}$-alkoxy,
    —C(O)(CH$_2$)$_q$OC(O)—C$_{1-12}$-alkyl,
    —C(O)(CH$_2$)$_q$NR$^i$R$^{ii}$,
    —C(O)O—C$_{1-12}$-alkyl, wherein alkyl is unsubstituted or substituted with one or more OH, halo, cyano or $C_{1-12}$-alkoxy,
    —S(O)$_2$—C$_{1-12}$-alkyl, or
    —S(O)$_2$NR$^i$R$^{ii}$,
  $R^i$ and $R^{ii}$ are each independently H, $C_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B,
  q is 1, 2, 3 or 4,
  r is 2, 3 or 4,
  A is halo, cyano, OH, $C_{1-7}$-alkyl, halo-$C_{1-7}$-alkyl, or $C_{1-7}$-alkoxy,
  B is oxo, halo, OH, $C_{1-7}$-alkyl or $C_{1-7}$alkoxy, and
  $R^3$ is Cl or F,
  or a pharmaceutically acceptable salt thereof.
2. The compound of claim 1, wherein
  $R^1$ is $C_{1-12}$-alkyl, unsubstituted or substituted with one or more halo, hydroxy or $C_{1-12}$-alkoxy,
    $C_{3-7}$ cycloalkyl, or
    4-7 membered heterocycloalkyl containing one or two heteroatoms selected from O and S, which heterocycloalkyl is unsubstituted or substituted by one or more oxo, halo, OH, $C_{1-7}$-alkyl or $C_{1-7}$-alkoxy.
3. The compound of claim 1, wherein $R^1$ is $C_{1-12}$-alkyl or $C_{3-7}$ cycloalkyl.
4. The compound of claim 1, wherein $R^1$ is —CF$_3$, —CH(CH$_3$)CH$_2$CF$_3$, —CH(CH$_3$)CH$_2$F, —CH(CH$_3$)CH$_2$OH, —CH(CH$_3$)CH$_2$OMe, cyclobutyl, cyclohexyl, cyclopentyl, ethyl, i-propyl, methyl, oxetanyl, sec-butyl, t-butyl or tetrahydro-pyranyl.
5. The compound of claim 4, wherein $R^1$ is i-propyl, cyclobutyl or cyclopentyl.
6. The compound of claim 1, wherein
  $R^2$ is H,
    $C_{1-12}$-alkyl, unsubstituted or substituted with one or more OH,
    —(CH$_2$)$_q$—R$^a$, wherein R$^a$ is phenyl or 5- or 6-membered heteroaryl and q is 1, 2, 3 or 4,
    —C(O)—C$_{1-12}$-alkyl, wherein alkyl is unsubstituted or substituted with one or more OH,
    —C(O)(CH$_2$)$_q$OC(O)—C$_{1-12}$-alkyl, wherein q is 1, 2, 3 or 4,
    —C(O)O—C$_{1-12}$-alkyl,
    —S(O)$_2$—C$_{1-12}$-alkyl, or
    —S(O)$_2$NR$^i$R$^{ii}$, wherein R$^i$ and R$^{ii}$ are each independently H or C$_{1-12}$-alkyl.
7. The compound of claim 6, wherein $R^2$ is $C_{1-12}$-alkyl.
8. The compound of claim 6, wherein $R^2$ is 2-hydroxyethyl, —C(O)CH$_2$OC(O)methyl, —C(O)hydroxymethyl, —C(O)methyl, —C(O)O-t-butyl, —CH$_2$-pyridin-2-yl, H, i-propyl, methyl, —S(O)$_2$-methyl or —S(O)$_2$N(methyl)$_2$.
9. The compound of claim 8, wherein $R^2$ is methyl.
10. The compound claim 1, wherein $R^3$ is Cl.
11. The compound of claim 1, wherein the compound is selected from
  trans-8-chloro-1-(4-ethoxy-cyclohexyl)-4H,6H-2,3,5,10b-tetraaza-benzo[e]azulene-5-carboxylic acid tert-butyl ester;
  trans-8-chloro-1-(4-ethoxy-cyclohexyl)-5-methyl-5,6-dihydro-4H-2,3,5,10b-tetraaza-benzo[e]azulene;

trans-8-chloro-1-(4-isopropoxy-cyclohexyl)-4H,6H-2,3,5,10b-tetraaza-benzo[e]azulene-5-carboxylic acid tert-butyl ester;

trans-8-chloro-1-(4-isopropoxy-cyclohexyl)-5-methyl-5,6-dihydro-4H-2,3,5,10b-tetraaza-benzo[e]azulene;

trans-8-chloro-1-(4-isopropoxy-cyclohexyl)-5-methanesulfonyl-5,6-dihydro-4H-2,3,5,10b-tetraaza-benzoazulene;

trans-2-[8-chloro-1-(4-isopropoxy-cyclohexyl)-4H,6H-2,3,5,10b-tetraaza-benzoazulen-5-yl]-ethanol;

trans-8-chloro-1-(4-isopropoxy-cyclohexyl)-5-isopropyl-5,6-dihydro-4H-2,3,5,10b-tetraaza-benzoazulene;

trans-8-chloro-1-(4-isopropoxy-cyclohexyl)-4H,6H-2,3,5,10b-tetraaza-benzoazulene-5-sulfonic acid dimethylamide;

trans-8-chloro-1-(4-isopropoxy-cyclohexyl)-5-pyridin-2-ylmethyl-5,6-dihydro-4H-2,3,5,10b-tetraaza-benzoazulene; and trans-acetic acid 2-[8-chloro-1-(4-isopropoxy-cyclohexyl)-4H,6H-2,3,5,10b-tetraaza-benzoazulen-5-yl]-2-oxo-ethyl ester.

12. The compound of claim 1, wherein the compound is selected from trans-1-[8-chloro-1-(4-isopropoxy-cyclohexyl)-4H,6H-2,3,5,10b-tetraaza-benzoazulen-5-yl]-2-hydroxy-ethanone;

trans-1-[8-chloro-1-(4-isopropoxy-cyclohexyl)-4H,6H-2,3,5,10b-tetraaza-benzoazulen-5-yl]-ethanone;

trans-8-fluoro-1-(4-isopropoxy-cyclohexyl)-4H,6H-2,3,5,10b-tetraaza-benzo[e]azulene-5-carboxylic acid tert-butyl ester;

cis-8-chloro-1-(4-isopropoxy-cyclohexyl)-4H,6H-2,3,5,10b-tetraaza-benzo[e]azulene-5-carboxylic acid tert-butyl ester;

(RS)-trans-1-(4-sec-butoxy-cyclohexyl)-8-chloro-4H,6H-2,3,5,10b-tetraaza-benzo[e]azulene-5-carboxylic acid tert-butyl ester;

(RS)-trans-1-(4-sec-butoxy-cyclohexyl)-8-chloro-5,6-dihydro-4H-2,3,5,10b-tetraaza-benzo[e]azulene hydrochloride;

(RS)-trans-1-(4-sec-butoxy-cyclohexyl)-8-chloro-5-methyl-5,6-dihydro-4H-2,3,5,10b-tetraaza-benzo[e]azulene;

(+)-trans-1-(4-sec-butoxy-cyclohexyl)-8-chloro-5-methyl-5,6-dihydro-4H-2,3,5,10b-tetraaza-benzo[e]azulene;

(−)-trans-1-(4-sec-butoxy-cyclohexyl)-8-chloro-5-methyl-5,6-dihydro-4H-2,3,5,10b-tetraaza-benzo[e]azulene; and trans-8-chloro-1-(4-cyclobutoxy-cyclohexyl)-4H,6H-2,3,5,10b-tetraaza-benzo[e]azulene-5-carboxylic acid tert-butyl ester.

13. The compound of claim 1, wherein the compound is selected from trans-8-chloro-1-(4-cyclobutoxy-cyclohexyl)-5,6-dihydro-4H-2,3,5,10b-tetraaza-benzo[e]azulene hydrochloride;

trans-8-chloro-1-(4-cyclobutoxy-cyclohexyl)-5-methyl-5,6-dihydro-4H-2,3,5,10b-tetraaza-benzo[e]azulene;

cis-8-chloro-1-(4-cyclobutoxy-cyclohexyl)-4H,6H-2,3,5,10b-tetraaza-benzo[e]azulene-5-carboxylic acid tert-butyl ester;

cis-8-chloro-1-(4-cyclobutoxy-cyclohexyl)-5-methyl-5,6-dihydro-4H-2,3,5,10b-tetraaza-benzo[e]azulene;

trans-8-chloro-1-(4-cyclopentyloxy-cyclohexyl)-4H,6H-2,3,5,10b-tetraaza-benzo[e]azulene-5-carboxylic acid tert-butyl ester;

trans-8-chloro-1-(4-cyclopentyloxy-cyclohexyl)-5,6-dihydro-4H-2,3,5,10b-tetraaza-benzo[e]azulene hydrochloride;

trans-8-chloro-1-(4-cyclopentyloxy-cyclohexyl)-5-methyl-5,6-dihydro-4H-2,3,5,10b-tetraaza-benzo[e]azulene;

trans-8-chloro-1-(4-cyclohexyloxy-cyclohexyl)-4H,6H-2,3,5,10b-tetraaza-benzoazulene-5-carboxylic acid tert-butyl ester;

trans-8-chloro-1-(4-cyclohexyloxy-cyclohexyl)-5-methyl-5,6-dihydro-4H-2,3,5,10b-tetraaza-benzoazulene; and (RS)-trans-8-chloro-1-[4-(2-methoxy-1-methyl-ethoxy)-cyclohexyl]-4H,6H-2,3,5,10b-tetraaza-benzo[e]azulene-5-carboxylic acid tert-butyl ester.

14. The compound of claim 1, wherein the compound is selected from (RS)-trans-8-chloro-1-[4-(2-methoxy-1-methyl-ethoxy)-cyclohexyl]-5-methyl-5,6-dihydro-4H-2,3,5,10b-tetraaza-benzo[e]azulene;

(−)-trans-8-chloro-1-[4-(2-methoxy-1-methyl-ethoxy)-cyclohexyl]-5-methyl-5,6-dihydro-4H-2,3,5,10b-tetraaza-benzo[e]azulene;

(RS)-trans-8-chloro-1-[4-(2-hydroxy-1-methyl-ethoxy)-cyclohexyl]-4H,6H-2,3,5,10b-tetraaza-benzo[e]azulene-5-carboxylic acid tert-butyl ester;

(RS)-trans-8-chloro-1-[4-(2-fluoro-1-methyl-ethoxy)-cyclohexyl]-5-methyl-5,6-dihydro-4H-2,3,5,10b-tetraaza-benzo[e]azulene;

(RS)-trans-8-chloro-1-[4-(3,3,3-trifluoro-1-methyl-propoxy)-cyclohexyl]-4H,6H-2,3,5,10b-tetraaza-benzo[e]azulene-5-carboxylic acid tert-butyl ester;

(RS)-trans-8-chloro-5-methyl-1-[4-(3,3,3-trifluoro-1-methyl-propoxy)-cyclohexyl]-5,6-dihydro-4H-2,3,5,10b-tetraaza-benzo[e]azulene;

trans-8-chloro-1-[4-(oxetan-3-yloxy)-cyclohexyl]-4H,6H-2,3,5,10b-tetraaza-benzo[e]azulene-5-carboxylic acid tert-butyl ester;

trans-8-chloro-1-[4-(tetrahydro-pyran-4-yloxy)-cyclohexyl]-4H,6H-2,3,5,10b-tetraaza-benzoazulene-5-carboxylic acid tert-butyl ester;

cis-8-chloro-1-[4-(tetrahydro-pyran-4-yloxy)-cyclohexyl]-4H,6H-2,3,5,10b-tetraaza-benzoazulene-5-carboxylic acid tert-butyl ester, and trans-1-(4-tert-butoxy-cyclohexyl)-8-chloro-4H,6H-2,3,5,10b-tetraaza-benzo[e]azulene-5-carboxylic acid tert-butyl ester.

15. The compound of claim 1, wherein the compound is selected from trans-8-chloro-1-(4-isopropoxy-cyclohexyl)-5-methyl-5,6-dihydro-4H-2,3,5,10b-tetraaza-benzo[e]azulene, trans-8-chloro-1-(4-cyclobutoxy-cyclohexyl)-5-methyl-5,6-dihydro-4H-2,3,5,10b-tetraaza-benzo[e]azulene, and trans-8-chloro-1-(4-cyclopentyloxy-cyclohexyl)-5-methyl-5,6-dihydro-4H-2,3,5,10b-tetraaza-benzo[e]azulene.

16. The compound of claim 15, wherein the compound is trans-8-chloro-1-(4-cyclopentyloxy-cyclohexyl)-5-methyl-5,6-dihydro-4H-2,3,5,10b-tetraaza-benzo[e]azulene.

17. A pharmaceutical composition comprising a therapeutically effective amount of a compound of formula I

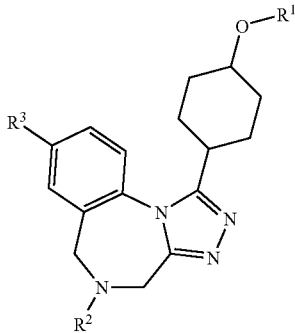

wherein
- $R^1$ is $C_{1-12}$-alkyl, unsubstituted or substituted with one or more halo, hydroxy, cyano or $C_{1-12}$-alkoxy,
  - $C_{3-7}$-cycloalkyl, unsubstituted or substituted by one or more substituents independently selected from B,
  - 4-7 membered heterocycloalkyl containing one or two heteroatoms selected from O, N and S, which heterocycloalkyl is unsubstituted or substituted by one or more substituents independently selected from B,
- $R^2$ is H,
  - $C_{1-12}$-alkyl, unsubstituted or substituted with one or more OH, halo, cyano or $C_{1-12}$-alkoxy,
  - —$(CH_2)_q$—$R^a$, wherein $R^a$ is phenyl or 5- or 6-membered heteroaryl, each of which is unsubstituted or substituted with one or more substituents independently selected from A,
  - —$(CH_2)_rNR^iR^{ii}$,
  - —$C(O)$—$C_{1-12}$-alkyl, wherein alkyl is unsubstituted or substituted with one or more OH, halo, cyano or $C_{1-12}$-alkoxy,
  - —$C(O)(CH_2)_qOC(O)$—$C_{1-12}$-alkyl,
  - —$C(O)(CH_2)_qNR^iR^{ii}$,
  - —$C(O)O$—$C_{1-12}$-alkyl, wherein alkyl is unsubstituted or substituted with one or more OH, halo, cyano or $C_{1-12}$-alkoxy,
  - —$S(O)_2$—$C_{1-12}$-alkyl, or
  - —$S(O)_2NR^iR^{ii}$,
- $R^i$ and $R^{ii}$ are each independently H, $C_{1-12}$-alkyl, or together with the nitrogen to which they are bound form a 3- to 7-membered heterocycloalkyl containing one or two heteroatoms selected from N, O and S, which heterocycloalkyl is unsubstituted or substituted by one or more substituents independently selected from B,
- q is 1, 2, 3 or 4,
- r is 2, 3 or 4,
- A is halo, cyano, OH, $C_{1-7}$-alkyl, halo-$C_{1-7}$-alkyl, or $C_{1-7}$-alkoxy,
- B is oxo, halo, OH, $C_{1-7}$-alkyl or $C_{1-7}$-alkoxy, and
- $R^3$ is Cl or F,
- or a pharmaceutically acceptable salt thereof and a pharmaceutically acceptable carrier.

* * * * *